US012617830B2

(12) United States Patent
Bloom

(10) Patent No.: US 12,617,830 B2
(45) Date of Patent: \*May 5, 2026

(54) ANALOGUES OF PYY

(71) Applicant: IP2IPO Innovations Limited, London (GB)

(72) Inventor: Stephen Robert Bloom, London (GB)

(73) Assignee: IP2IPO Innovations Limited, London (GB)

( \* ) Notice: Subject to any disclaimer, the term of this patent is extended or adjusted under 35 U.S.C. 154(b) by 0 days.

This patent is subject to a terminal disclaimer.

(21) Appl. No.: 18/524,472

(22) Filed: Nov. 30, 2023

(65) Prior Publication Data

US 2024/0166709 A1     May 23, 2024

Related U.S. Application Data

(62) Division of application No. 17/868,559, filed on Jul. 19, 2022, now Pat. No. 12,060,402, which is a division of application No. 16/769,760, filed as application No. PCT/GB2018/053513 on Dec. 4, 2018, now Pat. No. 11,421,012.

(30) Foreign Application Priority Data

Dec. 4, 2017     (GB) ..................................... 1720188

(51) Int. Cl.
| | |
|---|---|
| *C07K 14/575* | (2006.01) |
| *A61K 9/00* | (2006.01) |
| *A61K 38/17* | (2006.01) |
| *A61K 38/26* | (2006.01) |
| *A61K 38/00* | (2006.01) |

(52) U.S. Cl.
CPC ...... *C07K 14/57545* (2013.01); *A61K 9/0029* (2013.01); *A61K 38/00* (2013.01)

(58) Field of Classification Search
CPC . C07K 14/57545; A61K 9/0029; A61K 38/00
See application file for complete search history.

(56) References Cited

U.S. PATENT DOCUMENTS

| | | | |
|---|---|---|---|
| 4,179,337 | A | 12/1979 | Davis et al. |
| 5,700,486 | A | 12/1997 | Canal et al. |
| 5,936,092 | A | 8/1999 | Shen et al. |
| 5,939,380 | A | 8/1999 | Wang |
| 5,993,414 | A | 11/1999 | Haller |
| 6,093,692 | A | 7/2000 | Shen et al. |
| 6,225,445 | B1 | 5/2001 | Shen et al. |
| 6,355,478 | B1 | 3/2002 | Baez et al. |
| 6,410,707 | B2 | 6/2002 | Wagner et al. |
| 6,420,352 | B1 | 7/2002 | Knowles |
| 6,436,091 | B1 | 8/2002 | Harper et al. |
| 6,447,743 | B1 | 9/2002 | Devic et al. |
| 8,603,969 | B2 | 12/2013 | Levy et al. |
| 11,421,012 | B2 | 8/2022 | Bloom |
| 12,060,402 | B2 | 8/2024 | Bloom |
| 2006/0094653 | A1 | 5/2006 | Levy et al. |
| 2011/0021420 | A1 | 1/2011 | Bloom et al. |
| 2013/0023464 | A1 | 1/2013 | Bloom |
| 2017/0137486 | A1 | 5/2017 | Bloom |
| 2023/0126347 | A1 | 4/2023 | Bloom |

FOREIGN PATENT DOCUMENTS

| | | | |
|---|---|---|---|
| CN | 1124927 | A | 6/1996 |
| CN | 1301269 | A | 6/2001 |
| CN | 101203531 | A | 6/2008 |
| CN | 102741278 | A | 10/2012 |
| CN | 103459416 | A | 12/2013 |
| JP | 2013518090 | A | 5/2013 |
| WO | WO-9309227 | A1 | 5/1993 |
| WO | WO-03026591 | A2 | 4/2003 |
| WO | WO-2004062685 | A2 | 7/2004 |
| WO | WO-2005077094 | A2 | 8/2005 |
| WO | WO-2005089789 | A2 | 9/2005 |
| WO | WO-2006066024 | A2 | 6/2006 |
| WO | WO-2008003947 | A1 | 1/2008 |
| WO | WO-2011092473 | A1 | 8/2011 |
| WO | WO-2012006566 | A2 | 1/2012 |
| WO | WO-2012101413 | A1 | 8/2012 |
| WO | WO-2015177572 | A1 | 11/2015 |
| WO | WO-2019110982 | A1 | 6/2019 |

OTHER PUBLICATIONS

Donaldson et al., "The Prader-Willi syndrome", Archives of Disease in Childhood 70: 58-63 (1994) (Year: 1994).\*
Hirschberg, "Sex hormones, appetite and eating behaviour in women," Maturitas 71: 248-256 (2012) (Year: 2012).\*
Abid et al., "Complication and Management of Hypothyroidism—A Review," Indian Journal of Drugs 4:42-56 (2016) (Year: 2016).\*
Stice et al, "Neural Vulnerability Factors That Increase Risk for Future Weight Gain," Psychological Bulletin 142:447-471 (2016), manuscript version pp. 1-71 (Year: 2016).\*
Barlow, S. E. et al., "Obesity Evaluation and Treatment: Expert Committee Recommendations," Pediatrics, vol. 102, No. 3, Sep. 3, 1998, pp. 1-11.
Batterham, R. L. et al., "Gut hormone PYY3-36 physiologically inhibits food intake," letters to nature, Aug. 8, 2002, pp. 650-654, vol. 48.
Batterham, R. L. et al., "Inhibition of Food Intake in Obese Subjects by Peptide YY3-36," The New England Journal of Medicine, Sep. 4, 2003, pp. 941-948, vol. 349, No. 10.

(Continued)

*Primary Examiner* — Julie Ha
*Assistant Examiner* — Kristina M Hellman
(74) *Attorney, Agent, or Firm* — COOLEY LLP

(57)     ABSTRACT

Analogues of PYY differing from native human PYY by substitution of Ser23 with Ala23, Glu23, Lys23, Gln23 or AIB23. Further optional features include substitutions at further positions, loss of the Tyr1 residue of native human PYY and amidation of the C-terminus. Suitable for use as pharmaceuticals for treating and preventing disorders, in particular diabetes and obesity.

21 Claims, 21 Drawing Sheets

Specification includes a Sequence Listing.

(56)                    References Cited

OTHER PUBLICATIONS

Byrn, S. et al., "Pharmaceutical Solids: A Strategic Approach to Regulatory Considerations," Pharmaceutical Research, vol. 12, Iss. 7, Jul. 1995, pp. 945-954.

Centers for Disease Control and Prevention, "National Health and Nutrition Examination Survey: NHANES 2011-2012 Overview," Date Unknown, three pages, [Online] [Retrieved on Feb. 19, 2021] Retrieved from the Internet URL: https://www.cdc.gov/nchs/ nhanes/ conti n uousn ha nes/ overview.aspx?-BeginYear=2011.

De Silva, A. et al., "Gut Hormones and Appetite Control: A Focus on PYY and GLP-1 as Therapeutic Targets in Obesity," Gut and Liver, Jan. 2012, pp. 10-20, vol. 6, No. 1.

Druce, M.R. et al., "Investigation of Structure-Activity Relationships of Oxyntomodulin (Oxm) Using Oxm Analogs," Endocrinology, vol. 150, Iss. 4, Apr. 1, 2009, pp. 1712-1721.

Dumont, Y. et al., "Characterization of a Selective Neuropeptide Y/Peptide YYY2 Receptor Radioligand: [125I]PYY3-36," Society for Neuroscience Abstracts, 1993, one page, vol. 19 (abstract only).

EMedicine Health, diabetes causes, http://www.onhealth.com/ diabetes_health/page3.htm#diabetes_causes (referenced Aug. 22, 2013) (Year: 2013) 4 pages.

International Search Report and Written Opinion, Patent Cooperation Treaty Application No. PCT/GB2018/053513, dated Apr. 5, 2019, 17 Pages.

Kenchaiah, S. et al., "Obesity and the Risk of Heart Failure," The New England Journal of Medicine, vol. 347, No. 5, Aug. 1, 2002, pp. 305-313.

Kopelman, P.G., "Obesity as a medical problem," Nature, vol. 404, Apr. 6, 2000, pp. 635-643.

Langer, R. (Sep. 28, 1990) "New methods of drug delivery" Science, 249(4976):1527-1533.

Langer, R., "New methods of drug delivery," Science, vol. 249, Iss. 4976, Sep. 28, 1990, pp. 1527-1533.

Lyznicki, J.M. et al., "Obesity: assessment and management in primary care," Am Fam Physician 63(11), Jun. 2001, pp. 2185-2196.

Medlineplus, obesity, accessed 2013 (Year: 2013), 1 page.

National Institutes of Health, "Executive Summary," Obesity Research, vol. 6, Suppl. 2, Sep. 1998, pp. 515-1795.

Nishizawa, N., et al., "Antiobesity Effect of a Short-Length Peptide VY Analogue after Continuous Administration in Mice," ACS Medical. Chemistry Letters, 2017, vol. 8, No. 6, pp. 628-631.

Rissanen, A. et al., "Risk of disability and mortality due to overweight in a Finnish population," British Medical Journal, vol. 301, Oct. 13, 1990, pp. 835-837.

Saudek, CD. et al., "A preliminary trial of the programmable implantable medication system for insulin delivery," The New England Journal of Medicine 321(9), Aug. 31, 1989, pp. 574-579.

Sefton, M.V., "Implantable pumps," Critical Reviews in Biomedical Engineering, vol. 14, Iss. 3, 1987, pp. 201-240.

St. John Providence Health Center; Preventing Obesity, http://www. stjohnprovidence.org/HealthInfoLib/swarticle.aspx?type=85&id= P07863 (Year: 2013) 2 pages.

Tan, T., et al., "The Effect of a Subcutaneous Infusion of GLP-1, OXM, and PYY on Energy Intake and Expenditure in Obese Volunteers," Journal of Clinical Endocrinology Metabolism, 2017, vol. 102, No. 7, pp. 2364-2372.

United Healthcare, diabetes, http://www.uhc.com/source4women/ health_topics/diabetes/relatedinformation/ d0f0417b073bf110VgnVCM1000002f10b10a__.html referenced Aug. 22, 2013 (Year: 2013) 2 pages.

United Kingdom Intellectual Property Office, Combined Search and Examination Report, Application No. GB1720188.0, dated Sep. 3, 2018, eight pages.

Wang, Y. et al., "Parenteral Formulations of Proteins and Peptides: Stability and Stabilizers," Journal of Parenteral Science and Technology, Technical Report No. 10, Supplement 1988, vol. 42, No. 2S, pp. S2-S25.

Jequier, E., "Energy, obesity, and body weight standards," American Journal of Clinical Nutrition, vol. 45, May 1987, pp. 1035-1036.

* cited by examiner

FIG. 1A

| REF | | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| 1 | | Tyr | Pro | Ile | Lys | Pro | Glu | Ala | Pro | Gly | Glu | Asp | Ala | Ser | Pro | Glu | Glu | Leu | Asn |
| 17 | 1276 | | Pro | Ile | Lys | Pro | Glu | Ala | Pro | Gly | Lys | Gly | Ala | Ser | Pro | Glu | Glu | Ile | AiB |
| 18 | 1319 | | Pro | Ile | Lys | Pro | Glu | Ala | Pro | Gly | Lys | Gly | AiB | Ser | Pro | Glu | Glu | Ile | Ala |
| 19 | 1371 | | Pro | Ile | Lys | Pro | Glu | Ala | Pro | Gly | Glu | Gly | Ala | Ser | Pro | Glu | Glu | Ile | Leu |
| 20 | 1372 | | Pro | Ile | Lys | Pro | Glu | Ala | Pro | Gly | Glu | Gly | Ala | Ser | Pro | Glu | Glu | Ile | Leu |
| 21 | 1377 | | Pro | Ile | Lys | Pro | Glu | Ala | Pro | Gly | Glu | Gly | Ala | Ser | Pro | Glu | Glu | Ile | Leu |
| 22 | 1379 | | Pro | Ile | Lys | Pro | Glu | Ala | Pro | Gly | Glu | Gly | Ala | Ser | Pro | Glu | Glu | Ile | Leu |
| 23 | 1419 | | Pro | Ile | Lys | Pro | Glu | Ala | Pro | Gly | Glu | Gly | Ala | Ser | Pro | Glu | Glu | Leu | Leu |
| 24 | 1421 | | Pro | Ile | Lys | Pro | Glu | Ala | Pro | Gly | Gln | Gly | Ala | Ser | Pro | Glu | Glu | Leu | Leu |
| 25 | 1431 | | Pro | Ile | Lys | Pro | Glu | Ala | Pro | Gly | Glu | Gly | Ala | Ser | Pro | Glu | Glu | AiB | Leu |
| 26 | 1447 | | Pro | Ile | Lys | Pro | Glu | Ala | Pro | Gly | Gln | Gly | Ala | Ser | Pro | Glu | Glu | Ile | Leu |
| 27 | 1448 | | Pro | Ile | Lys | Pro | Glu | Ala | Pro | Gly | Lys | Gly | Ala | Ser | Pro | Glu | Glu | Ile | Leu |
| 28 | 1450 | | Pro | Ile | Lys | Pro | Glu | Ala | Pro | Gly | Glu | Gly | Ala | Ser | Pro | Glu | Glu | Ile | Leu |
| 29 | 1477 | | Pro | Ile | Lys | Pro | Glu | Ala | Pro | Gly | Glu | Gly | Ala | Ser | Pro | Glu | Glu | Ile | Leu |
| 30 | 1489 | | Pro | Ile | Lys | Pro | Glu | Ala | Pro | Gly | Gln | Gly | Ala | Ser | Pro | Glu | Glu | Ile | Leu |
| REF | | 1 | 2 | 3 | 4 | 5 | 6 | 7 | 8 | 9 | 10 | 11 | 12 | 13 | 14 | 15 | 16 | 17 | 18 |

FIG. 1B

| REF | | 19 | 20 | 21 | 22 | 23 | 24 | 25 | 26 | 27 | 28 | 29 | 30 | 31 | 32 | 33 | 34 | 35 | 36 | |
|---|---|---|---|---|---|---|---|---|---|---|---|---|---|---|---|---|---|---|---|---|
| 1 | | Arg | Tyr | Tyr | Ala | Ser | Leu | Arg | His | Tyr | Leu | Asn | Leu | Val | Thr | Arg | Gln | Arg | Tyr | |
| 17 | 1276 | Arg | Tyr | Tyr | Val | Glu | Leu | Arg | His | Phe | Leu | Asn | His | Leu | Thr | Arg | Gln | Arg | Tyr | NH2 |
| 18 | 1319 | His | Tyr | Tyr | Ala | Ala | Leu | Arg | His | Phe | Leu | Asn | His | Leu | Thr | Arg | Gln | Arg | Tyr | NH2 |
| 19 | 1371 | His | Tyr | Tyr | Ala | Ala | Leu | Arg | His | Phe | Leu | Asn | His | Leu | Thr | Arg | Gln | Arg | Tyr | NH2 |
| 20 | 1372 | His | Tyr | Tyr | Ala | AiB | Leu | Arg | His | Phe | Leu | Asn | His | Leu | Thr | Arg | Gln | Arg | Tyr | NH2 |
| 21 | 1377 | His | Tyr | Tyr | Ala | Ser | Leu | Arg | His | Phe | Leu | Asn | His | Leu | Thr | Arg | Gln | Arg | Tyr | NH2 |
| 22 | 1379 | His | Tyr | Tyr | Ala | Gln | Leu | Arg | His | Phe | Leu | Asn | His | Leu | Thr | Arg | Gln | Arg | Tyr | NH2 |
| 23 | 1419 | His | Tyr | Tyr | Ala | Ala | Leu | Arg | His | Phe | Leu | Asn | His | Val | Thr | Arg | Gln | Arg | Tyr | NH2 |
| 24 | 1421 | His | Tyr | Tyr | Ala | Ala | Leu | Arg | His | Phe | Leu | Asn | His | Val | Thr | Arg | Gln | Arg | Tyr | NH2 |
| 25 | 1431 | Lys | Tyr | Tyr | Ile | Glu | Leu | Arg | His | Phe | Leu | Asn | His | Leu | Thr | Arg | Gln | Arg | Tyr | NH2 |
| 26 | 1447 | Lys | Tyr | Tyr | Ile | Glu | Leu | Arg | His | Phe | Leu | Asn | His | Leu | Thr | Arg | Gln | Arg | Tyr | NH2 |
| 27 | 1448 | Lys | Tyr | Tyr | Ile | Glu | Leu | Arg | His | Phe | Leu | Asn | His | Leu | Thr | Arg | Gln | Arg | Tyr | NH2 |
| 28 | 1450 | Lys | Tyr | Tyr | Ile | Glu | Leu | Arg | His | Phe | Leu | Asn | His | Leu | Thr | Arg | Gln | Arg | Tyr | NH2 |
| 29 | 1477 | Arg | Tyr | Tyr | Ala | Ala | Leu | Arg | His | Phe | Leu | Asn | His | Leu | Thr | Arg | Gln | Arg | Tyr | NH2 |
| 30 | 1489 | His | Tyr | Tyr | Val | Glu | Leu | Arg | His | Phe | Leu | Asn | His | Leu | Thr | Arg | Gln | Arg | Tyr | NH2 |
| REF | | 19 | 20 | 21 | 22 | 23 | 24 | 25 | 26 | 27 | 28 | 29 | 30 | 31 | 32 | 33 | 34 | 35 | 36 | |

FIG. 1C

| REF | | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| 1 | | Tyr | Pro | Ile | Lys | Pro | Glu | Ala | Pro | Gly | Glu | Asp | Ala | Ser | Pro | Glu | Glu | Leu | Asn |
| 31 | 1490 | | Pro | Ile | Lys | Pro | Glu | Ala | Pro | Gly | Gln | Gly | Ala | Ser | Pro | Glu | Glu | Ile | Leu |
| 32 | 1518 | | Pro | Ile | Lys | Pro | Glu | Ala | Pro | Gly | Glu | Gly | Ala | Ser | Pro | Glu | Glu | Leu | Leu |
| 33 | 1528 | | Pro | Ile | Lys | Pro | Glu | Ala | Pro | Gly | Glu | Gly | Ala | Ser | Pro | Glu | Glu | Ile | Leu |
| 34 | 1553 | | Pro | Ile | Lys | Pro | Glu | Ala | Pro | Gly | Ala | Gly | Ala | Ser | Pro | Glu | Glu | Ile | Leu |
| 35 | 1558 | | Pro | Ile | Lys | Pro | Glu | Ala | Pro | Gly | Glu | Gly | Ala | Ser | Pro | Glu | Glu | Ile | Leu |
| 36 | 1568 | | Pro | Ile | Lys | Pro | Glu | Ala | Pro | Gly | Glu | Gly | Ala | Ser | Pro | Glu | Glu | Ile | Leu |
| 37 | 1572 | | Pro | Ile | Lys | Pro | Glu | Ala | Pro | Gly | Glu | Gly | Ala | Ser | Pro | Glu | Glu | Leu | Leu |
| 38 | 1576 | | Pro | Ile | Lys | Pro | Glu | Ala | Pro | Gly | Gln | Gly | Ala | Ser | Pro | Glu | Glu | Leu | Leu |
| 39 | 1577 | | Pro | Ile | Lys | Pro | Glu | Ala | Pro | Gly | Glu | Gly | Ala | Ser | Pro | Glu | Glu | AiB | Leu |
| 40 | 1578 | | Pro | Ile | Lys | Pro | Glu | Ala | Pro | Gly | Glu | Gly | Ala | Ser | Pro | Glu | Glu | Leu | Leu |
| 41 | 1579 | | Pro | Ile | Lys | Pro | Glu | Ala | Pro | Gly | Lys | Gly | AiB | Ser | Pro | Glu | Glu | Ile | Ala |
| 42 | 1580 | | Pro | Ile | Lys | Pro | Glu | Ala | Pro | Gly | Glu | Gly | Ala | Ser | Pro | Glu | Glu | Ile | Leu |
| 43 | 1581 | | Pro | Ile | Lys | Pro | Glu | Ala | Pro | Gly | Glu | Gly | Ala | Ser | Pro | Glu | Glu | Ile | Leu |
| REF | | 1 | 2 | 3 | 4 | 5 | 6 | 7 | 8 | 9 | 10 | 11 | 12 | 13 | 14 | 15 | 16 | 17 | 18 |

FIG. 1D

| REF |      | 19  | 20  | 21  | 22  | 23  | 24  | 25  | 26  | 27  | 28  | 29  | 30  | 31  | 32  | 33  | 34  | 35  | 36  |      |
|-----|------|-----|-----|-----|-----|-----|-----|-----|-----|-----|-----|-----|-----|-----|-----|-----|-----|-----|-----|------|
| 1   |      | Arg | Tyr | Tyr | Ala | Ser | Leu | Arg | His | Tyr | Leu | Asn | Leu | Val | Thr | Arg | Gln | Arg | Tyr | NH2  |
| 31  | 1490 | Lys | Tyr | Tyr | Val | Glu | Leu | Arg | His | Phe | Leu | Asn | His | Leu | Thr | Arg | Gln | Arg | Tyr | NH2  |
| 32  | 1518 | His | Tyr | Tyr | Ala | Ala | Leu | Arg | His | Phe | Leu | Asn | His | Leu | Thr | Arg | Gln | Arg | Tyr | NH2  |
| 33  | 1528 | Arg | Tyr | Tyr | Ile | Ala | Leu | Arg | His | Phe | Leu | Asn | His | Leu | Thr | Arg | Gln | Arg | Tyr | NH2  |
| 34  | 1553 | His | Tyr | Tyr | Ala | Lys | Leu | Arg | His | Phe | Leu | Asn | His | Val | Thr | Arg | Gln | Arg | Tyr | NH2  |
| 35  | 1558 | His | Tyr | Tyr | Ala | Ala | Leu | Arg | His | Tyr | Leu | Asn | His | Leu | Thr | Arg | Gln | Arg | Tyr | NH2  |
| 36  | 1568 | His | Tyr | Tyr | Ala | Ala | Leu | Arg | His | Phe | Leu | Asn | His | Leu | Thr | Arg | Gln | Arg | Tyr | NH2  |
| 37  | 1572 | His | Tyr | Tyr | Ala | Ala | Leu | Arg | His | Phe | Leu | Asn | His | Val | Thr | Arg | Gln | Arg | Tyr | NH2  |
| 38  | 1576 | His | Tyr | Tyr | Ala | Ala | Leu | Arg | His | Phe | Leu | Asn | His | Val | Thr | Arg | Gln | Arg | Tyr | NH2  |
| 39  | 1577 | Lys | Tyr | Tyr | Ile | Glu | Leu | Arg | His | Phe | Leu | Asn | His | Leu | Thr | Arg | Gln | Arg | Tyr | NH2  |
| 40  | 1578 | His | Tyr | Tyr | Ala | Ala | Leu | Arg | His | Phe | Leu | Asn | His | Leu | Thr | Arg | Gln | Arg | Tyr | NH2  |
| 41  | 1579 | His | Tyr | Tyr | Ala | Ala | Leu | Arg | His | Phe | Leu | Asn | His | Leu | Thr | Arg | Gln | Arg | Tyr | NH2  |
| 42  | 1580 | His | Tyr | Tyr | Ala | AiB | Leu | Arg | His | Phe | Leu | Asn | His | Leu | Thr | Arg | Gln | Arg | Tyr | NH2  |
| 43  | 1581 | Arg | Tyr | Tyr | Ile | Ala | Leu | Arg | His | Phe | Leu | Asn | His | Leu | Thr | Arg | Gln | Arg | Tyr | NH2  |
| REF |      | 19  | 20  | 21  | 22  | 23  | 24  | 25  | 26  | 27  | 28  | 29  | 30  | 31  | 32  | 33  | 34  | 35  | 36  |      |

SEQUENCE LISTING

```
Sequence total quantity: 44
SEQ ID NO: 1               moltype = AA  length = 36
FEATURE                    Location/Qualifiers
source                     1..36
                           mol_type = protein
                           organism = Homo sapiens
SEQUENCE: 1
YPIKPEAPGE DASPEELNRY YASLRHYLNL VTRQRY                               36

SEQ ID NO: 2               moltype = AA  length = 34
FEATURE                    Location/Qualifiers
source                     1..34
                           mol_type = protein
                           organism = Homo sapiens
SEQUENCE: 2
IKPEAPGEDA SPEELNRYYA SLRHYLNLVT RQRY                                 34

SEQ ID NO: 3               moltype = AA  length = 36
FEATURE                    Location/Qualifiers
source                     1..36
                           mol_type = protein
                           organism = Rattus norvegicus
SEQUENCE: 3
YPAKPEAPGE DASPEELSRY YASLRHYLNL VTRQRY                               36

SEQ ID NO: 4               moltype = AA  length = 36
FEATURE                    Location/Qualifiers
source                     1..36
                           mol_type = protein
                           organism = Mus musculus
SEQUENCE: 4
YPAKPEAPGE DASPEELSRY YASLRHYLNL VTRQRY                               36

SEQ ID NO: 5               moltype = AA  length = 36
FEATURE                    Location/Qualifiers
source                     1..36
                           mol_type = protein
                           organism = Sus scrofa
SEQUENCE: 5
YPAKPEAPGE DASPEELSRY YASLRHYLNL VTRQRY                               36

SEQ ID NO: 6               moltype = AA  length = 36
FEATURE                    Location/Qualifiers
source                     1..36
                           mol_type = protein
                           organism = Cavia porcellus
SEQUENCE: 6
YPSKPEAPGS DASPEELARY YASLRHYLNL VTRQRY                               36

SEQ ID NO: 7               moltype = AA  length = 36
FEATURE                    Location/Qualifiers
source                     1..36
                           mol_type = protein
                           organism = Rana temporaria
SEQUENCE: 7
YPPKPENPGE DASPEEMTKY LTALRHYINL VTRQRY                               36

SEQ ID NO: 8               moltype = AA  length = 36
FEATURE                    Location/Qualifiers
source                     1..36
                           mol_type = protein
                           organism = Raja sp.
SEQUENCE: 8
YPPKPENPGD DAAPEELAKY YSALRHYINL ITRQRY                               36

SEQ ID NO: 9               moltype = AA  length = 36
FEATURE                    Location/Qualifiers
source                     1..36
                           mol_type = protein
                           organism = Squalus acanthias
SEQUENCE: 9
YPPKPENPGE DAPPEELAKY YSALRHYINL ITRQRY                               36

SEQ ID NO: 10              moltype = AA  length = 36
FEATURE                    Location/Qualifiers
source                     1..36
                           mol_type = protein
                           organism = Lampetra sp.
```

-continued

```
SEQUENCE: 10
FPPKPDNPGD NASPEQMARY KAAVRHYINL ITRQRY                                   36

SEQ ID NO: 11           moltype = AA  length = 36
FEATURE                 Location/Qualifiers
source                  1..36
                        mol_type = protein
                        organism = Petromyzon sp.
SEQUENCE: 11
MPPKPDNPSP DASPEELSKY MLAVRNYINL ITRQRY                                   36

SEQ ID NO: 12           moltype = AA  length = 36
FEATURE                 Location/Qualifiers
source                  1..36
                        mol_type = protein
                        note = Canis lupus familiaris
                        organism = Canis lupus
SEQUENCE: 12
YPAKPEAPGE DASPEELSRY YASLRHYLNL VTRQRY                                   36

SEQ ID NO: 13           moltype = AA  length = 36
FEATURE                 Location/Qualifiers
source                  1..36
                        mol_type = protein
                        organism = Macaca mulatta
SEQUENCE: 13
YPIKPEAPGE DASPEELSRY YASLRHYLNL VTRQRY                                   36

SEQ ID NO: 14           moltype = AA  length = 36
FEATURE                 Location/Qualifiers
source                  1..36
                        mol_type = protein
                        organism = Xenopus tropicalis
SEQUENCE: 14
YPTKPENPGN DASPEEMAKY LTALRHYINL VTRQRY                                   36

SEQ ID NO: 15           moltype = AA  length = 36
FEATURE                 Location/Qualifiers
source                  1..36
                        mol_type = protein
                        organism = Salmo salar
SEQUENCE: 15
YPPKPENPGE DAPPEELAKY YTALRHYINL ITRQRY                                   36

SEQ ID NO: 16           moltype = AA  length = 36
FEATURE                 Location/Qualifiers
source                  1..36
                        mol_type = protein
                        organism = Bos taurus
SEQUENCE: 16
YPAKPQAPGE HASPDELNRY YTSLRHYLNL VTRQRF                                   36

SEQ ID NO: 17           moltype = AA  length = 35
FEATURE                 Location/Qualifiers
REGION                  1..35
                        note = PYY analogue
MOD_RES                 17
                        note = Aib
MOD_RES                 35
                        note = AMIDATION
source                  1..35
                        mol_type = protein
                        organism = synthetic construct
SEQUENCE: 17
PIKPEAPGKG ASPEEIXRYY VELRHFLNHL TRQRY                                    35

SEQ ID NO: 18           moltype = AA  length = 35
FEATURE                 Location/Qualifiers
REGION                  1..35
                        note = PYY analogue
MOD_RES                 11
                        note = Aib
MOD_RES                 35
                        note = AMIDATION
source                  1..35
                        mol_type = protein
                        organism = synthetic construct
SEQUENCE: 18
PIKPEAPGKG XSPEEIAHYY AALRHFLNHL TRQRY                                    35
```

-continued

```
SEQ ID NO: 19          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 19
PIKPEAPGEG ASPEEILHYY AALRHFLNHL TRQRY                           35

SEQ ID NO: 20          moltype = AA  length = 35
FEATURE                Location/Qualifiers
REGION                 1..35
                       note = PYY analogue
MOD_RES                22
                       note = Aib
MOD_RES                35
                       note = AMIDATION
source                 1..35
                       mol_type = protein
                       organism = synthetic construct
SEQUENCE: 20
PIKPEAPGEG ASPEEILHYY AXLRHFLNHL TRQRY                           35

SEQ ID NO: 21          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 21
PIKPEAPGEG ASPEEILHYY ASLRHFLNHL TRQRY                           35

SEQ ID NO: 22          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 22
PIKPEAPGEG ASPEEILHYY AQLRHFLNHL TRQRY                           35

SEQ ID NO: 23          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 23
PIKPEAPGEG ASPEELLHYY AALRHFLNHV TRQRY                           35

SEQ ID NO: 24          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 24
PIKPEAPGQG ASPEELLHYY AALRHFLNHV TRQRY                           35

SEQ ID NO: 25          moltype = AA  length = 35
FEATURE                Location/Qualifiers
REGION                 1..35
                       note = PYY analogue
```

-continued

```
MOD_RES              16
                     note = Aib
MOD_RES              35
                     note = AMIDATION
source               1..35
                     mol_type = protein
                     organism = synthetic construct
SEQUENCE: 25
PIKPEAPGEG ASPEEXLKYY IELRHFLNHL TRQRY                                    35

SEQ ID NO: 26        moltype = AA   length = 35
FEATURE              Location/Qualifiers
REGION               1..35
                     note = PYY analogue
MOD_RES              35
                     note = AMIDATION
source               1..35
                     mol_type = protein
                     organism = synthetic construct
SEQUENCE: 26
PIKPEAPGQG ASPEEILKYY IELRHFLNHL TRQRY                                    35

SEQ ID NO: 27        moltype = AA   length = 35
FEATURE              Location/Qualifiers
REGION               1..35
                     note = PYY analogue
MOD_RES              35
                     note = AMIDATION
source               1..35
                     mol_type = protein
                     organism = synthetic construct
SEQUENCE: 27
PIKPEAPGKG ASPEEILKYY IELRHFLNHL TRQRY                                    35

SEQ ID NO: 28        moltype = AA   length = 35
FEATURE              Location/Qualifiers
REGION               1..35
                     note = PYY analogue
MOD_RES              35
                     note = AMIDATION
source               1..35
                     mol_type = protein
                     organism = synthetic construct
SEQUENCE: 28
PIKPEAPGEG ASPEEILKYY IELRHFLNHL TRQRY                                    35

SEQ ID NO: 29        moltype = AA   length = 35
FEATURE              Location/Qualifiers
REGION               1..35
                     note = PYY analogue
MOD_RES              35
                     note = AMIDATION
source               1..35
                     mol_type = protein
                     organism = synthetic construct
SEQUENCE: 29
PIKPEAPGEG ASPEEILRYY AALRHFLNHL TRQRY                                    35

SEQ ID NO: 30        moltype = AA   length = 35
FEATURE              Location/Qualifiers
REGION               1..35
                     note = PYY analogue
MOD_RES              35
                     note = AMIDATION
source               1..35
                     mol_type = protein
                     organism = synthetic construct
SEQUENCE: 30
PIKPEAPGQG ASPEEILHYY VELRHFLNHL TRQRY                                    35

SEQ ID NO: 31        moltype = AA   length = 35
FEATURE              Location/Qualifiers
REGION               1..35
                     note = PYY analogue
MOD_RES              35
                     note = AMIDATION
source               1..35
                     mol_type = protein
                     organism = synthetic construct
```

-continued

```
SEQUENCE: 31
PIKPEAPGQG ASPEEILKYY VELRHFLNHL TRQRY                                      35

SEQ ID NO: 32          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 32
PIKPEAPGEG ASPEELLHYY AALRHFLNHL TRQRY                                      35

SEQ ID NO: 33          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 33
PIKPEAPGEG ASPEEILRYY IALRHFLNHL TRQRY                                      35

SEQ ID NO: 34          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 34
PIKPEAPGAG ASPEEILHYY AKLRHFLNHV TRQRY                                      35

SEQ ID NO: 35          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 35
PIKPEAPGEG ASPEEILHYY AALRHYLNHL TRQRY                                      35

SEQ ID NO: 36          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 36
PIKPEAPGEG ASPEEILHYY AALRHFLNHL TRQRY                                      35

SEQ ID NO: 37          moltype = AA  length = 35
FEATURE                Location/Qualifiers
REGION                 1..35
                       note = PYY analogue
MOD_RES                35
                       note = AMIDATION
source                 1..35
                       mol_type = protein
                       organism = synthetic construct
SEQUENCE: 37
PIKPEAPGEG ASPEELLHYY AALRHFLNHV TRQRY                                      35

SEQ ID NO: 38          moltype = AA  length = 35
FEATURE                Location/Qualifiers
REGION                 1..35
                       note = PYY analogue
```

-continued

```
MOD_RES                  35
                         note = AMIDATION
source                   1..35
                         mol_type = protein
                         organism = synthetic construct
SEQUENCE: 38
PIKPEAPGQG ASPEELLHYY AALRHFLNHV TRQRY                                35

SEQ ID NO: 39            moltype = AA   length = 35
FEATURE                  Location/Qualifiers
REGION                   1..35
                         note = PYY analogue
MOD_RES                  16
                         note = Aib
MOD_RES                  35
                         note = AMIDATION
source                   1..35
                         mol_type = protein
                         organism = synthetic construct
SEQUENCE: 39
PIKPEAPGEG ASPEEXLKYY IELRHFLNHL TRQRY                                35

SEQ ID NO: 40            moltype = AA   length = 35
FEATURE                  Location/Qualifiers
REGION                   1..35
                         note = PYY analogue
MOD_RES                  35
                         note = AMIDATION
source                   1..35
                         mol_type = protein
                         organism = synthetic construct
SEQUENCE: 40
PIKPEAPGEG ASPEELLHYY AALRHFLNHL TRQRY                                35

SEQ ID NO: 41            moltype = AA   length = 35
FEATURE                  Location/Qualifiers
REGION                   1..35
                         note = PYY analogue
MOD_RES                  11
                         note = Aib
MOD_RES                  35
                         note = AMIDATION
source                   1..35
                         mol_type = protein
                         organism = synthetic construct
SEQUENCE: 41
PIKPEAPGKG XSPEEIAHYY AALRHFLNHL TRQRY                                35

SEQ ID NO: 42            moltype = AA   length = 35
FEATURE                  Location/Qualifiers
REGION                   1..35
                         note = PYY analogue
MOD_RES                  22
                         note = Aib
MOD_RES                  35
                         note = AMIDATION
source                   1..35
                         mol_type = protein
                         organism = synthetic construct
SEQUENCE: 42
PIKPEAPGEG ASPEEILHYY AXLRHFLNHL TRQRY                                35

SEQ ID NO: 43            moltype = AA   length = 35
FEATURE                  Location/Qualifiers
REGION                   1..35
                         note = PYY analogue
MOD_RES                  35
                         note = AMIDATION
source                   1..35
                         mol_type = protein
                         organism = synthetic construct
SEQUENCE: 43
PIKPEAPGEG ASPEEILRYY IALRHFLNHL TRQRY                                35

SEQ ID NO: 44            moltype = AA   length = 35
FEATURE                  Location/Qualifiers
REGION                   1..35
                         note = PYY analogue
MOD_RES                  35
```

-continued

```
                        note = AMIDATION
source                  1..35
                        mol_type = protein
                        organism = synthetic construct
SEQUENCE: 44
PIHPHAPGED ASPEELNHYY AALRHYLNHV TRQRY                    35
```

ANALOGUES OF PYY

CROSS-REFERENCE TO RELATED APPLICATIONS

This application is a divisional application of U.S. application Ser. No. 17/868,559, filed Jul. 19, 2022, which is a divisional of U.S. application Ser. No. 16/769,760, filed Jun. 4, 2020, now U.S. Pat. No. 11,421,012, issued Aug. 23, 2022, which is the National Stage of International Application No. PCT/GB2018/053513, filed Dec. 4, 2018, which claims the benefit of and priority to Great Britain Patent Application No. 1720188.0, filed Dec. 4, 2017, the contents of which are incorporated by reference in their entirety.

SEQUENCE LISTING

The instant application contains a Sequence Listing which has been submitted in XML format via EFS-Web and is hereby incorporated by reference in its entirety. Said XML copy, Dec. 2, 2023, is named METS_016_03US_SubSeqList_ST26.xml, and is 63,623 bytes in size.

FIELD OF THE INVENTION

This application relates to analogues of peptide YY (PYY), which are useful in treating disorders such as diabetes and obesity, either alone or in combination with other agents, especially in combination with GLP-1 analogues.

BACKGROUND OF THE INVENTION

According to the National Health and Nutrition Examination Survey (NHANES, 2011 to 2012), over two thirds of adults in the United States are overweight or obese. In the United States, 78% percent of males and 74% percent of women, of the age of 20 or older, are either overweight or obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type-2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., *N. Engl. J. Med.* 347:305, 2002; Massie, *N. Engl. J. Med.* 347:358, 2002). In addition, there is substantial evidence that weight loss in obese persons reduces important disease risk factors. Even a small weight loss, such as 10% of the initial body weight in both overweight and obese adults has been associated with a decrease in risk factors such as hypertension, hyperlipidemia, and hyperglycemia.

Although diet and exercise provide a simple process to decrease weight gain, overweight and obese individuals often cannot sufficiently control these factors to effectively lose weight. Pharmacotherapy is available; several weight loss drugs have been approved by the Food and Drug Administration that can be used as part of a comprehensive weight loss program. However, many of these drugs have serious adverse side effects. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients. It is not only obese subjects who wish to lose weight. People with weight within the recommended range, for example, in the upper part of the recommended range, may wish to reduce their weight, to bring it closer to the ideal weight. Thus, a need remains for agents that can be used to effect weight loss in overweight and obese subjects.

PYY is a 36-amino acid peptide produced by the L cells of the gut, with highest concentrations found in the large bowel and the rectum. Two endogenous forms, PYY and PYY 3-36, are released into the circulation. PYY 3-36 is further produced by cleavage of the Tyr-Pro amino terminal residues of PYY by the enzyme dipeptidyl peptidase IV (DPP-IV). PYY 3-36 binds to the Y2 receptor of the Y family of receptors (De Silva and Bloom, Gut Liver, 2012, 6, p 10-20). Studies have shown that peripheral administration of PYY 3-36 to rodents and humans leads to marked inhibition of food intake, leading to the prospect that analogues of PYY may be useful in treating conditions such as obesity (see, e.g. Batterham et al, Nature, 2002, 418, p 650-654; Batterham et al, New England Journal of Medicine, 2003, 349, p 941-948).

PYY has also been implicated in altering the metabolism of subjects and has been proposed as a treatment for type-2 diabetes, following evidence that it is able to restore impaired insulin and glucagon secretion in type-2 diabetes. The relationship between obesity and diabetes is complex because being overweight increases diabetic risk and being diabetic increases the likelihood of being overweight. The nexus between the two conditions is one in which PYY plays an increasingly recognized role.

WO2011/092473 and WO2012/101413 (Imperial Innovations Limited) disclose certain analogues of PYY. However, there remains a need for further compounds which have suitable properties so that they are effective as therapeutic agents in treating or preventing disorders of energy metabolism such as obesity and/or diabetes.

SUMMARY OF THE INVENTION

In a first aspect, the invention provides an analogue of PYY which differs from the sequence of native human PYY (Tyr1 Pro2 Ile3 Lys4 Pro5 Glu6 Ala7 Pro8 Gly9 Glu10 Asp11 Ala12 Ser13 Pro14 Glu15 Glu16 Leu17 Asn18 Arg19 Tyr20 Tyr21 Ala22 Ser23 Leu24 Arg25 His26 Tyr27 Leu28 Asn29 Leu30 Val31 Thr32 Arg33 Gln34 Arg35 Tyr36; SEQ ID NO: 1) in the following respect:

Ser23 is substituted with Ala23, Glu23, Lys23, Gln23 or AIB23 (preferably Ala23) and which may further differ from the sequence of native human PYY in one of more of the following further respects:

Tyr1 is absent, one or more of residues 2 to 9, 13 to 16, 20, 21, 24, 25 or 26 are subject to a conservative substitution, Glu10 is substituted with Ala10, Lys10 or Gln10

Asp11 is substituted with Gly11

Ala12 is substituted with AIB12

US 12,617,830 B2

3

Leu17 is substituted with Ile17 or AIB17
Asn18 is substituted with Leu18, AIB18 or Ala18
Arg19 is substituted with His19 or Lys19
Ala22 is substituted with Val22 or Ile22
Tyr27 is substituted with Phe27
Leu30 is substituted with His30
Val31 is substituted with Leu31
and wherein the C-terminal residue optionally terminates in a primary amide (—C(O)NH$_2$) group in place of a carboxylic acid group (—CO$_2$H);
or a derivative of the compound; or a salt of the compound or the derivative.

The present invention is based on the discovery that analogues of PYY in which specific amino acid residues are deleted and/or substituted can also be administered to a subject in order to cause decreased food intake, decreased caloric intake, decreased appetite and an alteration in energy metabolism. In many cases the PYY analogues of the present invention exhibit improved potency and/or longer duration of action and/or fewer side effects than native PYY.

The PYY analogues of the present invention are also especially suitable for use in combination therapies with agonists of the GLP-1 receptor. This is because PYY and GLP-1 analogues have broadly compatible and similar chemistries which lend them to being formulated in combination, so they can be conveniently administered as a single injection. Additionally, PYY analogues and GLP-1 analogues inhibit appetite by different and separate mechanisms, and so a patient receiving a combination therapy is less liable to 'escape' the desired pharmaceutical effect than would be the case if treated with either agent alone. Lastly, the different mechanisms of action allow for an additive or synergistic effect on appetite suppression, making a more potent therapy In another aspect, the invention provides a pharmaceutical composition comprising an analogue of PYY according to the invention together with a pharmaceutically acceptable carrier and optionally a further therapeutic agent.

In another aspect, the invention provides an analogue of PYY according to the invention, or a pharmaceutical composition comprising the PYY analogue, for use as a medicament. The analogue of PYY or pharmaceutical composition find use in the prevention or treatment of a disorder of energy metabolism such as diabetes and/or obesity, for use in preventing loss of pancreatic islet function and/or for use in recovering pancreatic islet function, in a subject.

In another aspect, the invention provides use of an analogue of PYY according to the invention for the manufacture of a medicament for the prevention or treatment of a disorder of energy metabolism such as diabetes and/or obesity, for preventing loss of pancreatic islet function and/or for recovering pancreatic islet function, in a subject.

In another aspect, the invention provides a method of treating or preventing a disease or disorder or other non-desired physiological state in a subject, comprising administering a therapeutically effective amount of an analogue of PYY according to the invention, or a pharmaceutical composition comprising the PYY analogue, to the subject. The analogue of PYY or pharmaceutical composition find use in methods for preventing or treating a disorder of energy metabolism such as diabetes and/or obesity, preventing loss of pancreatic islet function and/or recovering pancreatic islet function, reducing appetite, reducing food intake, and/or reducing calorie intake in a subject.

In another aspect, the invention also provides a method of causing weight loss or preventing weight gain in a subject for cosmetic purposes, comprising administering an effective amount of an analogue of PYY according to the invention, or a composition comprising the PYY analogue, to the subject.

BRIEF DESCRIPTION OF THE DRAWINGS

FIGS. 1A-1D are tables listing the amino acid sequences of some PYY analogues that relate to specific preferred embodiments of the invention. The naturally occurring sequence of human PYY is included for reference. The first column headed "REF" gives the SEQ ID NO: used in the accompanying sequence listing. Native human PYY is REF=1.

Figures 5A, 5B:
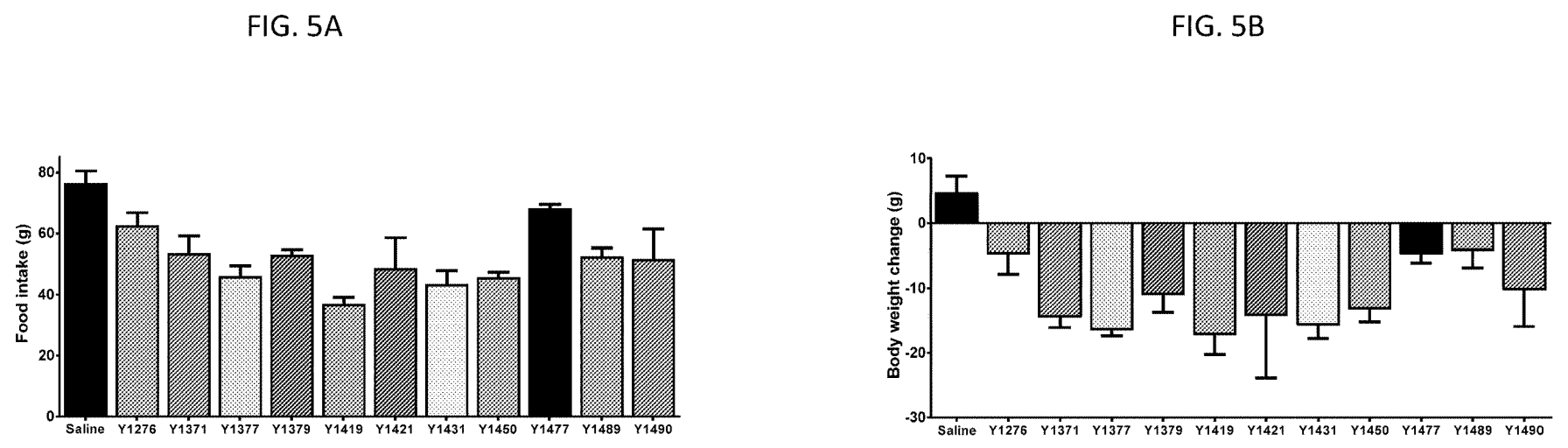

FIGS. 5A-5D show the results of an in vivo experiment demonstrating efficacy of other compounds of the invention

SEQUENCE LISTING

Figure 2:
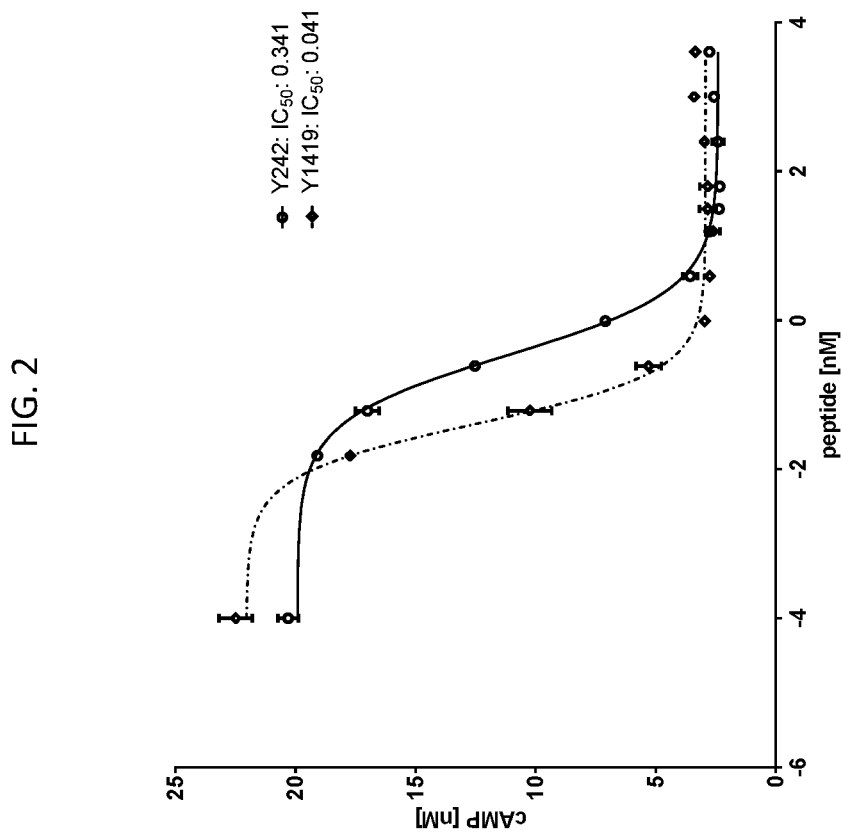
FIG. 2 shows the results of an in vitro receptor potency experiment described in the examples
Figure 3B:
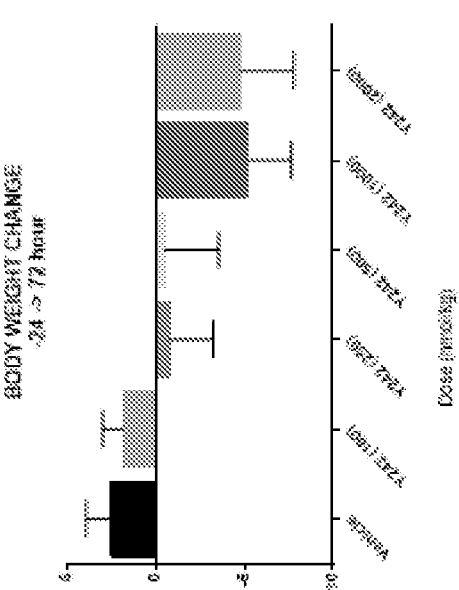
FIGS. 3A-3D show the results of an in vivo experiment (n=5 to 8) demonstrating efficacy of compound Y242 as described in the examples.
Figure 3A:
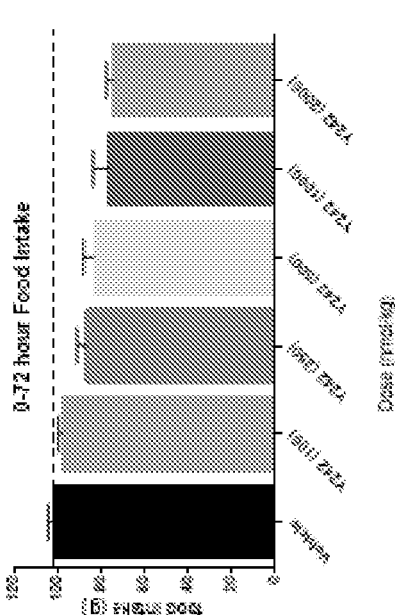
Figure 3D:
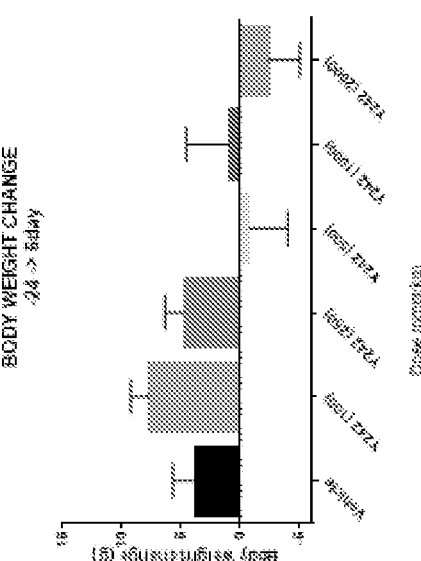
Figure 3C:
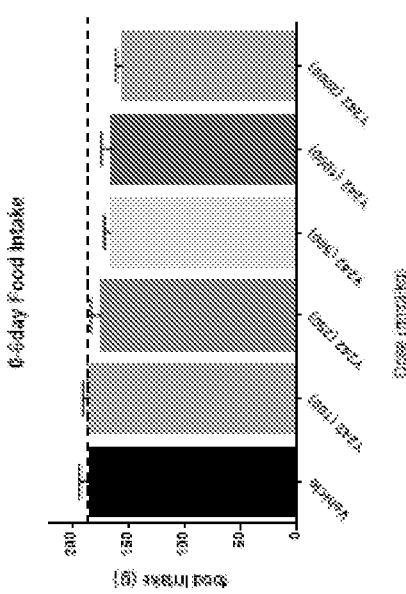
Figure 4B:
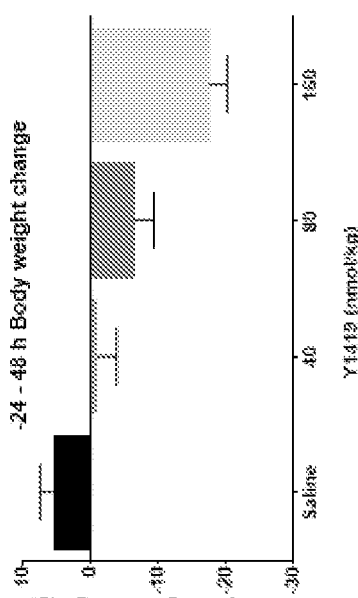
FIGS. 4A-4D show the results of an in vivo experiment (n=7 to 8) demonstrating efficacy of compound Y1419 as described in the examples.
Figure 4A:
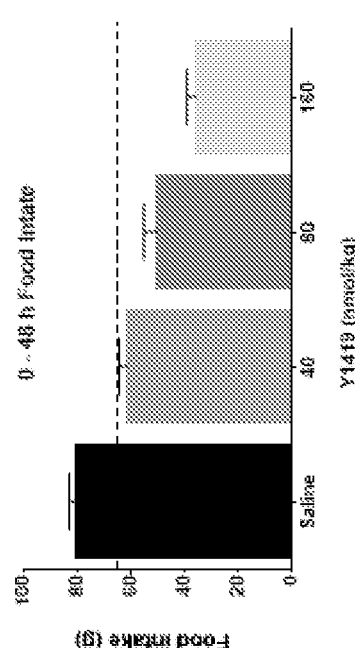
Figure 4D:
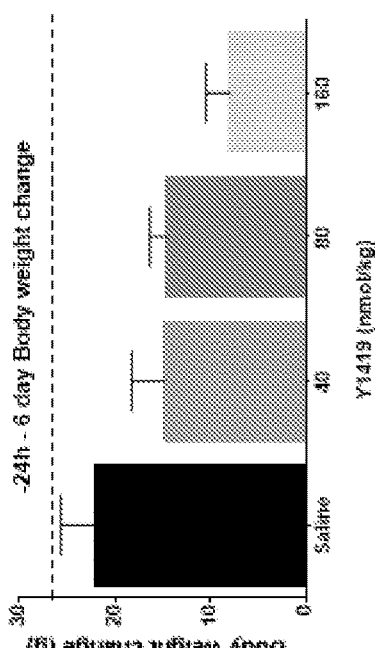
Figure 4C:
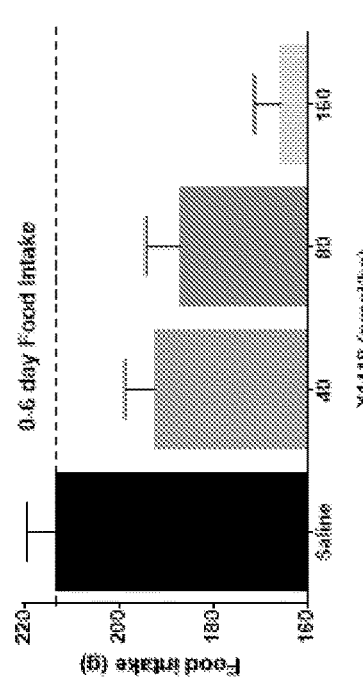
Figure 5D:
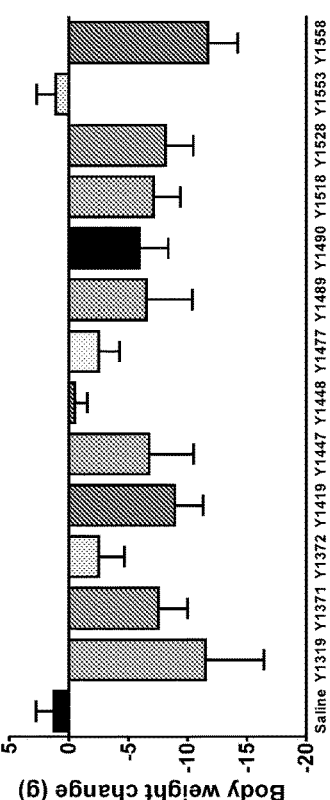
Figure 5C:
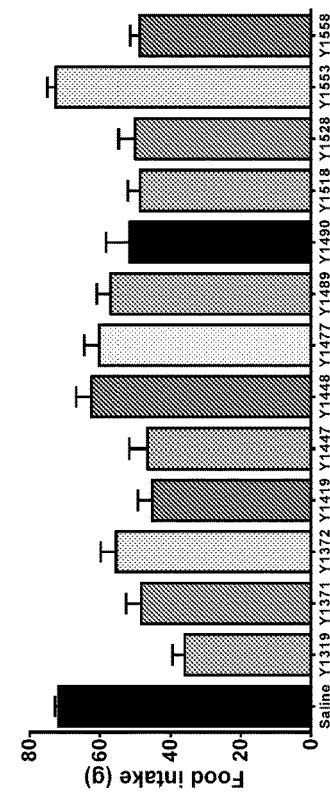

The amino acid sequences listed in the application are shown using standard letter abbreviations for amino acids. The specific sequences given herein relate to specific preferred embodiments of the invention. The application comprises a machine-readable sequence listing wherein PYY analogues are allocated SEQ ID NO identifiers which are the same as the Example numbers given in FIGS. 1A-1D.

Definitions

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Appetite: A natural desire, or longing for food. In one embodiment, appetite is measured by a survey to assess the desire for food. Increased appetite generally leads to increased feeding behavior.

Appetite Suppressants: Compounds that decrease the desire for food. Commercially available appetite suppressants include, but are not limited to, amfepramone (diethylpropion), phentermine, mazindol, phenylpropanolamine fenfluramine, dexfenfluramine, and fluoxetine.

Body Mass Index (BMI): A mathematical formula for measuring body mass, also sometimes called Quetelet's Index. BMI is calculated by dividing weight (in kg) by height$^2$ (in meters$^2$). The current standards for both men and women accepted as "normal" are a BMI of 20-24.9 kg/m$^2$. In one embodiment, a BMI of greater than 25 kg/m$^2$ can be used to identify an obese subject. Grade I obesity corresponds to a BMI of 25-29.9 kg/m$^2$. Grade II obesity corresponds to a BMI of 30-40 kg/m$^2$; and Grade III obesity corresponds to a BMI greater than 40 kg/m$^2$ (Jequier, *Am. J*

5

*Clin. Nutr.* 45:1035-47, 1987). Ideal body weight will vary among species and individuals based on height, body build, bone structure, and sex.

Conservative substitutions: The replacement of an amino acid residue by another, biologically similar residue in a polypeptide. The term "conservative variation" also includes the use of a substituted amino acid, i.e. an amino acid with one or more atoms replaced with another atom or group, in place of a parent amino acid provided that the polypeptide retains its activity or provided that antibodies raised to the substituted polypeptide also immunoreact with the unsubstituted polypeptide. Typical but not limiting conservative substitutions are the replacements, for one another, among the aliphatic amino acids Ala, Val, Leu and Ile; interchange of hydroxyl-containing residues Ser and Thr, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met and Gly. Additional conservative substitutions include the replacement of an amino acid by another of similar spatial or steric configuration, for example the interchange of Asn for Asp, or Gln for Glu.

Non-Limiting Examples of Conservative Amino Acid Substitutions

| Original Residue | Conservative Substitutions |
| --- | --- |
| Ala | Gly, Val, Leu, Ile, Ser, Thr, Met |
| Arg | Lys |
| Asn | Asp, Gln, His |
| Asp | Glu, Asn |
| Cys | Ser |
| Gln | Asn, His, Lys, Glu |
| Glu | Asp, Gln |
| Gly | Ala, Ser, Thr, Met |
| His | Asn, Gln |
| Ile | Ala, Leu, Val, Met |
| Leu | Ala, Ile, Val, Met, |
| Lys | Arg |
| Met | Leu, Ile, Ala, Ser, Thr, Gly |
| Phe | Leu, Tyr, Trp |
| Ser | Thr, Cys, Ala, Met, Gly |
| Thr | Ser, Ala, Ser, Met, Gly |
| Trp | Tyr, Phe |
| Tyr | Trp; Phe |
| Val | Ala, Ile, Leu |

Non-conservative substitutions: The replacement, in a polypeptide, of an amino acid residue by another residue which is not biologically similar. For example, the replacement of an amino acid residue with another residue that has a substantially different charge, a substantially different hydrophobicity or a substantially different spatial or steric configuration.

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterized by an inability to deliver insulin in an amount and with the precise timing that is needed for control of glucose homeostasis. Diabetes type I, or insulin dependent diabetes mellitus (IDDM) is caused by the destruction of β cells, which results in insufficient levels of endogenous insulin. Diabetes type II, or non-insulin dependent diabetes, results from a defect in both the body's sensitivity to insulin, and a relative deficiency in insulin production.

Food intake: The amount of food consumed by an individual. Food intake can be measured by volume or by weight. For example, food intake may be the total amount of food consumed by an individual. Or, food intake may be the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102:E29, 1998; National Institutes of Health, National Heart, Lung, and Blood Institute (NHLBI), *Obes. Res.* 6 (suppl. 2):51S-209S, 1998). Excess body fat is a result of an imbalance of energy intake and energy expenditure. For example, the Body Mass Index (BMI) may be used to assess obesity. In one commonly used convention, a BMI of 25.0 $kg/m^2$ to 29.9 $kg/m^2$ is overweight, while a BMI of 30 $kg/m^2$ or greater is obese.

In another convention, waist circumference is used to assess obesity. In this convention, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type-2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

Overweight: An individual who weighs more than their ideal body weight. An overweight individual can be obese, but is not necessarily obese. For example, an overweight individual is any individual who desires to decrease their weight. In one convention, an overweight individual is an individual with a BMI of 25.0 kg/m$^2$ to 29.9 kg/m$^2$.

Pegylated and pegylation: the process of reacting a poly (alkylene glycol), preferably an activated poly(alkylene glycol) to form a covalent bond. A facilitator may be used, for example an amino acid, e.g. lysine. Although "pegylation" is isoelectric focusing which is an electrophoretic method that utilises a pH gradient contained within a polyacrylimide gel.

Peptide YY (PYY): The term PYY as used herein refers to a peptide YY polypeptide, a hormone secreted into the blood by cells lining the lower small intestine (the ileum) and the colon. Naturally occurring wild type PYY sequences for various species are shown in Table 1.

TABLE 1

| PYY sequence of various species | |
| --- | --- |
| PEPTIDE YY | AA SEQUENCE |
| Human | YPIKPEAPGEDASPEELNRYYASLRHYLNLVTRQRY (SEQ ID NO: 1) |
| Human 3-36 | IKPEAPGEDASPEELNRYYASLRHYLNLVTRQRY (SEQ ID NO: 2) |
| Rat (*Rattus norvegicus*) | YPAKPEAPGEDASPEELSRYYASLRHYLNLVTRQRY (SEQ ID NO: 3) |
| Mouse (*Mus musculus*) | YPAKPEAPGEDASPEELSRYYASLRHYLNLVTRQRY (SEQ ID NO: 4) |
| Pig | YPAKPEAPGEDASPEELSRYYASLRHYLNLVTRQRY (SEQ ID NO: 5) |
| Guinea pig | YPSKPEAPGSDASPEELARYYASLRHYLNLVTRQRY (SEQ ID NO: 6) |
| Frog | YPPKPENPGEDASPEEMTKYLTALRHYINLVTRQRY (SEQ ID NO: 7) |
| Raja | YPPKPENPGDDAAPEELAKYYSALRHYINLITRQRY (SEQ ID NO: 8) |
| Dogfish | YPPKPENPGEDAPPEELAKYYSALRHYINLITRQRY (SEQ ID NO: 9) |
| Lampetra | FPPKPDNPGDNASPEQMARYKAAVRHYINLITRQRY (SEQ ID NO: 10) |
| Petromyzon | MPPKPDNPSPDASPEELSKYMLAVRNYINLITRQRY (SEQ ID NO: 11) |
| Dog (*Canis familiaris*) | YPAKPEAPGEDASPEELSRYYASLRHYLNLVTRQRY (SEQ ID NO: 12) |
| Rhesus monkey (*Macaca mulatta*) | YPIKPEAPGEDASPEELSRYYASLRHYLNLVTRQRY (SEQ ID NO: 13) |
| Pipid frog (*Xenopus tropicalis*) | YPTKPENPGNDASPEEMAKYLTALRHYINLVTRQRY (SEQ ID NO: 14) |
| Atlantic salmon (*Salmo salar*) | YPPKPENPGEDAPPEELAKYYTALRHYINLITRQRY (SEQ ID NO: 15) |
| Cattle (*bos taurus*) | YPAKPQAPGEHASPDELNRYYTSLRHYLNLVTRQRF (SEQ ID NO: 16) | often carried out using poly(ethylene glycol) or derivatives thereof, such as methoxy poly(ethylene glycol), the term is not limited herein to the use of methoxy poly(ethylene glycol) but also includes the use of any other useful poly (alkylene glycol), for example poly(propylene glycol).

pI: pI is an abbreviation for isoelectric point. An alternative abbreviation sometimes used is IEP. It is the pH at which a particular molecule carries no net electric charge. At a pH below its pI a protein or peptide carries a net positive charge. At a pH above its pI a protein or peptide carries a net negative charge. Proteins and peptides can be separated according to their isoelectric points using a technique called Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein encompass any amino acid sequence and include modified sequences such as glycoproteins. The term "polypeptide" is specifically covers naturally occurring proteins, as well as those which are recombinantly or synthetically produced. The term "polypeptide fragment" refers to a portion of a polypeptide, for example a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Subcutaneous administration: Subcutaneous administration is administration of a substance to the subcutaneous layer of fat which is found between the dermis of the skin and the underlying tissue. Subcutaneous administration may be by an injection using a hypodermic needle fitted, for example, to a syringe or a "pen" type injection device. Other administration methods may be used for example microneedles. Injection with a hypodermic needle typically involves a degree of pain on behalf of the recipient. Such pain may be masked by use of a local anaesthetic or analgesic. However, the usual method used to reduce the perceived pain of injections is to merely distract the subject immediately prior to and during the injection. Pain may be minimised by using a relatively small gauge hypodermic needle, by injecting a relatively small volume of substance and by avoiding excessively acidic or alkali compositions which may cause the subject to experience a "stinging" sensation at the injection site. Compositions having a pH of between pH4 and pH10 are usually regarded as tolerably comfortable.

Therapeutically effective amount: A dose sufficient to prevent advancement, or to cause regression of a disorder, or which is capable of relieving a sign or symptom of a disorder, or which is capable of achieving a desired result. In several embodiments, a therapeutically effective amount of a compound of the invention is an amount sufficient to inhibit or halt weight gain, or an amount sufficient to decrease appetite, or an amount sufficient to reduce caloric intake or food intake or increase energy expenditure.

DETAILED DESCRIPTION

According to a first aspect of the invention there is provided an analogue of PYY which differs from the sequence of native human PYY (Tyr1 Pro2 Ile3 Lys4 Pro5 Glu6 Ala7 Pro8 Gly9 Glu10 Asp11 Ala12 Ser13 Pro14 Glu15 Glu16 Leu17 Asn18 Arg19 Tyr20 Tyr21 Ala22 Ser23 Leu24 Arg25 His26 Tyr27 Leu28 Asn29 Leu30 Val31 Thr32 Arg33 Gln34 Arg35 Tyr36; SEQ ID NO:1) in the following respect:

Ser23 is substituted with Ala23, Glu23, Lys23, Gln23 or AIB23 (preferably Ala23) and which may further differ from the sequence of native human PYY in one of more of the following further respects:

Tyr1 is absent, one or more of residues 2 to 9, 13 to 16, 20, 21, 24, 25 or 26 (preferably, residues 11, 18, 19, 23, 27 and 30 or at least residues 11, 18, 19, 23, 27 and 30, or at least 4 or 5 of residues selected from 11, 18, 19, 23, 27 and 30) are subject to a conservative substitution, Glu10 is substituted with Ala10, Lys10 or Gln10

Asp11 is substituted with Gly11

Ala12 is substituted with AIB12

Leu17 is substituted with Ile17 or AIB17

Asn18 is substituted with AIB18, Ala18 or Leu18 (preferably Leu18)

Arg19 is substituted with His19 or Lys19 (preferably His19)

Ala22 is substituted with Val22 or Ile22

Tyr27 is substituted with Phe27

Leu30 is substituted with His30

Val31 is substituted with Leu31 and wherein the C-terminal residue optionally terminates in a primary amide (—C(O)NH$_2$) group in place of a carboxylic acid group (—CO$_2$H);

or a derivative of the compound; or a salt of the compound or the derivative.

The amino acid sequence of formula (I) above is shown with the N-terminus to the top left and the C-terminus to the bottom right. Unless indicated otherwise, the amino acid residues in the sequence of formula (I) are L-amino acids.

In one preferred embodiment, Tyr1 is absent. The removal of Tyr1 increases the selectivity of a PYY analogue for the Y2 receptor over the Y1 receptor, agonism of the Y2 receptor being responsible for the inhibition of feeding.

In one preferred embodiment residues 2 to 9 are unsubstituted.

In another preferred embodiment residues 2 to 9 are unsubstituted and Tyr1 is absent.

In another embodiment Tyr1 is absent, residues 2 to 9 are unsubstituted and Glu10 is substituted with Lys10.

In another embodiment Tyr1 is absent, residues 2 to 9 are unsubstituted and Glu10 is substituted with Gln10.

In another especially preferred embodiment Tyr1 is absent and residues 2 to 10 are unsubstituted.

According to one embodiment

Tyr1 is absent residues 2 to 9, 13 to 16, 20, 21, 24, 25, 26, 28, 29, 32, 33, 34 and 35 are unsubstituted.

According to one especially preferred embodiment:

Tyr1 is absent residues 2 to 10, 12 to 17, 20 to 22, 24 to 26, 28, 29 and 31 to 36 are unsubstituted.

Optionally, residue 14 may also be unsubstituted.

According to one embodiment:

Glu10 is substituted with Lys10 or Gln10

Asp11 is substituted with Gly11

Residue 12 is unsubstituted

Leu17 is unsubstituted

Asn18 is substituted with AIB18, Ala18 or Leu18

Arg19 is substituted with His19

Ala22 is unsubstituted

Ser23 is substituted with Glu23, Ala23, AIB 23 or Gln23

Tyr 27 is substituted with Phe27

Leu30 is substituted with His30

Val31 is substituted with Leu31.

According to one embodiment:

Tyr1 is absent

Glu10 is substituted with Lys10 or Gln10

Asp11 is substituted with Gly11

Residue 12 is unsubstituted

Leu17 is unsubstituted

Asn18 is substituted with AIB18, Ala18 or Leu18

Arg19 is substituted with His19

Ala22 is unsubstituted

Ser23 is substituted with Glu23, Ala23, AIB 23 or Gln23

Tyr 27 is substituted with Phe27

Leu30 is substituted with His30

Val31 is substituted with Leu31.

According to one embodiment:

Tyr1 is absent

Glu10 is substituted with Lys10 or Gln10

Asp11 is substituted with Gly11

Residues 2 to 9, 12 to 17, 20, 21, 24, 25, 26, 28, 29, 32, 33, 34 and 35 are unsubstituted Asn18 is substituted with AIB18, Ala18 or Leu18
Arg19 is substituted with His19
Ala22 is unsubstituted
Ser23 is substituted with Glu2, Ala23, AIB 23 or Gln23
Tyr 27 is substituted with Phe27
Leu30 is substituted with His30
Val31 is substituted with Leu31.
According to one embodiment:
Tyr1 is absent
Glu10 is substituted with Lys10 or Gln10
Asp11 is substituted with Gly11
Residues 2 to 9, 12 to 17, 20, 21, 24, 25, 26, 28, 29, 32, 33, 34 and 35 are unsubstituted
Asn18 is substituted with AIB18, Ala18 or Leu18
Arg19 is substituted with His19
Ala22 is unsubstituted
Ser23 is substituted with Glu23, Ala23, AIB 23 or Gln23
Tyr 27 is substituted with Phe27
Leu30 is substituted with His30
Val31 is substituted with Leu31
the C-terminal residue terminates in a primary amide (—C(O)NH$_2$) group in place of a carboxylic acid group (—CO$_2$H).
According to one embodiment:
Glu10 is unsubstituted
Asp11 is substituted with Gly11
Residue 12 is unsubstituted
Leu17 is unsubstituted
Asn18 is unsubstituted
Arg19 is His19
Ala22 is unsubstituted
Ser23 is substituted with Ala23
Tyr27 is substituted with Phe27
Leu30 is substituted with His30
Val31 is substituted with Leu31
the C-terminal residue terminates in a primary amide (—C(O)NH$_2$) group in place of a carboxylic acid group (—CO$_2$H).
According to one embodiment:
Tyr1 is absent
Glu10 is unsubstituted
Asp11 is substituted with Gly11
Residue 12 is unsubstituted
Leu17 is unsubstituted
Asn18 is unsubstituted
Arg19 is His19
Ala22 is unsubstituted
Ser23 is substituted with Ala23
Tyr27 is substituted with Phe27
Leu30 is substituted with His30
Val31 is substituted with Leu31
the C-terminal residue terminates in a primary amide (—C(O)NH$_2$) group in place of a carboxylic acid group (—CO$_2$H); optionally all of residues 2 to 9, 12 to 17, 20, 21, 24, 25, 26, 28, 29, 32, 33, 34 and 35 are unsubstituted.
In some embodiments Asp11 is substituted with Gly11.
In some embodiments Asn18 is substituted with AIB18, Ala18 or Leu18, preferably Leu18.
According to one embodiment:
Glu10 is substituted with Lys10 or Gln10
Asp11 is substituted with Gly11
Residue 12 is unsubstituted
Leu17 is unsubstituted
Asn18 is substituted with Leu18
Arg19 is substituted with His19
Ala22 is unsubstituted Ser23 is substituted with Glu23, Ala23, AIB 23 or Gln23
Tyr 27 is substituted with Phe27
Leu30 is substituted with His30
Val31 is substituted with Leu31.
According to one embodiment:
Tyr1 is absent
Glu10 is substituted with Lys10 or Gln10
Asp11 is substituted with Gly11
Residue 12 is unsubstituted
Leu17 is unsubstituted
Asn18 is substituted with Leu18
Arg19 is substituted with His19
Ala22 is unsubstituted
Ser23 is substituted with Glu23, Ala23, AIB 23 or Gln23
Tyr 27 is substituted with Phe27
Leu30 is substituted with His30
Val31 is substituted with Leu31.
According to one embodiment:
Tyr1 is absent
Glu10 is substituted with Lys10 or Gln10
Asp11 is substituted with Gly11
Residues 2 to 9, 12 to 17, 20, 21, 24, 25, 26, 28, 29, 32, 33, 34 and 35 are unsubstituted
Asn18 is substituted with Leu18
Arg19 is substituted with His19
Ala22 is unsubstituted
Ser23 is substituted with Glu23, Ala23, AIB 23 or Gln23
Tyr 27 is substituted with Phe27
Leu30 is substituted with His30
Val31 is substituted with Leu31.
According to one embodiment:
Tyr1 is absent
Glu10 is substituted with Lys10 or Gln10
Asp11 is substituted with Gly11
Residues 2 to 9, 12 to 17, 20, 21, 24, 25, 26, 28, 29, 32, 33, 34 and 35 are unsubstituted
Asn18 is substituted with Leu18
Arg19 is substituted with His19
Ala22 is unsubstituted
Ser23 is substituted with Glu23, Ala23, AIB 23 or Gln23
Tyr 27 is substituted with Phe27
Leu30 is substituted with His30
Val31 is substituted with Leu31
the C-terminal residue terminates in a primary amide (—C(O)NH$_2$) group in place of a carboxylic acid group (—CO$_2$H).
According to one embodiment:
Glu10 is unsubstituted
Asp11 is substituted with Gly11
Residue 12 is unsubstituted
Leu17 is unsubstituted
Asn18 is substituted with Leu18
Arg19 is His19
Ala22 is unsubstituted
Ser23 is substituted with Ala23
Tyr27 is substituted with Phe27
Leu30 is substituted with His30
Val31 is substituted with Leu31
the C-terminal residue terminates in a primary amide (—C(O)NH$_2$) group in place of a carboxylic acid group (—CO$_2$H).
According to one embodiment:
Tyr1 is absent
Glu10 is unsubstituted
Asp11 is substituted with Gly11
Residue 12 is unsubstituted
Leu17 is unsubstituted Asn18 is substituted with Leu18

Arg19 is His19

Ala22 is unsubstituted

Ser23 is substituted with Ala23

Tyr27 is substituted with Phe27

Leu30 is substituted with His30

Val31 is substituted with Leu31 the C-terminal residue terminates in a primary amide ($—C(O)NH_2$) group in place of a carboxylic acid group ($—CO_2H$)

optionally all of residues 2 to 9, 12 to 17, 20, 21, 24, 25, 26, 28, 29, 32, 33, 34 and 35 are unsubstituted.

According to one embodiment:

Tyr1 is absent

Residues 2 to 10, 12 to 17, 20, 21, 22, 24, 25, 26, 28, 29, 31, 32, 33, 34, 35 and 36 are unsubstituted Asp11 is substituted with Gly11

Asn18 is substituted with Leu18

Arg19 is substituted with His19

Ser23 is substituted with Ala23

Tyr 27 is substituted with Phe27

Leu30 is substituted with His30

Val31 is substituted with Leu31 the C-terminal residue terminates in a primary amide ($—C(O)NH_2$) group in place of a carboxylic acid group ($—CO_2H$).

According to one preferred embodiment at least 9 of the following 10 criteria apply:

1—Tyr 1 is absent

2—residues 2 to 10, 12 to 17, 20, 21, 22, 24, 25, 26, 28, 29, 31, 32, 33, 34, 35 and 36 are unsubstituted 3—Asp11 is substituted with Gly11

4—Asn18 is substituted with Leu18

5—Arg19 is substituted with His19

6—Ser23 is substituted with Ala23

7—Tyr27 is substituted with Phe27

8—Leu30 is substituted with His30

9—Val31 is unsubstituted

10—the C-terminal residue terminates in a primary amide ($—C(O)NH_2$) group in place of a carboxylic acid group ($—CO_2H$).

The invention contemplates embodiments above, wherein at least criteria 1 and 2 and at least 7 other criteria apply, or where criteria 1, 2 and 10 and at least 6 other criteria apply, or where all criteria 1 to 10 apply.

According to some embodiments Leu30 is substituted with His30.

According to some embodiments Val31 is unsubstituted.

According to certain embodiments, the naturally occurring Pro residues at positions 2, 5, 8 and 14 are retained. It has been found that these residues form hydrogen bonds which are important in stabilizing the tertiary structure of the molecule. Accordingly, according to certain preferred embodiments, there is provided an analogue of PYY which differs from the sequence of native human PYY in the following respects:

Ser23 is substituted with Ala23, Glu23, Lys23, Gln23 or AIB23 (preferably Ala23)

Such a compound may further differ from the sequence of native human PYY in one or more of the following respects:

Tyr is absent

One or more residues 3, 4, 6, 7, 9, 13, 15, 16, 20, 21, 24, 25 or 26 are subject to a conservative substitution, Glu10 is substituted with Ala10, Lys10 or Gln10

Asp11 is substituted with Gly11

Ala12 is substituted with AIB12

Leu17 is substituted with Ile17 or AIB17

Asn18 is substituted with AIB18, Ala18 or Leu18 (preferably Leu18)

Arg19 is substituted with His19 or Lys19 (preferably His19)

Ala22 is substituted with Val22 or Ile22

Tyr27 is substituted with Phe27

Leu30 is substituted with His30

Val31 is substituted with Leu31 and wherein the C-terminal residue optionally terminates in a primary amide ($—C(O)NH_2$) group in place of a carboxylic acid group ($—CO_2H$);

or a derivative of the compound; or a salt of the compound or the derivative.

According to all embodiments it is preferred that the C-terminal residue terminates in a primary amide group ($—C(O)NH_2$) in place of a carboxylic acid group ($—CO_2H$). The absence of the amide group results in a significant decrease in agonism of the Y2 receptor.

According to all embodiments Ser23 is substituted for an alternative amino acid residue. Although a substitution at position 23 has previously been disclosed as a tolerated change from the native sequence, previous PYY analogues which contained position 23 substitutions (for example Y242 disclosed in the applicant's previous patent applications) did not exhibit the same advantages as peptides of the present invention as shown in the comparative studies presented herein.

According to some embodiments Ser23 is substituted with Glu23, Ala23, AIB23 or Gln23.

Preferred specific sequences include the sequences disclosed herein and in particular those identified as Y1319, Y1371, Y1372, Y1419, Y1421, Y1518, Y1528, Y1558, Y1568, Y1572, Y1579, Y1553 or Y1581 (and especially Y1419). The invention encompasses, as preferred sequences, sequences corresponding to those of Y1319, Y1371, Y1372, Y1419, Y1421, Y1518, Y1528, Y1558, Y1568, Y1572, Y1579, Y1553 or Y1581 (and especially Y1419) to which 1 or 2 substitutions (for example conservative substitutions have been made) and which retain the activity (for example at least 20, 50 or 70% of the activity in one of the assays disclosed herein) of the sequence on which it is based.

According to a further aspect of the invention there is provided a pharmaceutical composition comprising an analogue of PYY according to the invention together with a pharmaceutically acceptable carrier and optionally a further therapeutic agent.

The second therapeutic agent may be an anti-obesity agent, an appetite suppressant or an anti-diabetic agent. Preferably the therapeutic agent is an analogue of GLP-1 or an analogue of glucagon or a derivative of either thereof.

According to certain embodiments discussed further below the composition comprises $Zn^{2+}$ ions.

According to another aspect of the invention there is provided an analogue of PYY according to the invention or a pharmaceutical composition according to the invention for use as a medicament.

According to certain embodiments the medicament is for the prevention or treatment of a disorder of energy metabolism, such as diabetes and/or obesity or for preventing loss of pancreatic islet function or for recovering pancreatic islet function.

According to certain embodiments the medicament is for use in preventing diabetes or obesity in a subject.

According to a further aspect of the invention there is provided a method of treating or preventing a disease or disorder or other non-desired physiological state in a subject comprising administering a therapeutically acceptable/effective amount of an analogue of PYY according to the invention, or a pharmaceutical composition, according to the invention, to the subject.

According to a further aspect of the invention there is provided a method of preventing or treating a disorder of energy metabolism such as diabetes and/or obesity, preventing loss of pancreatic islet function and/or recovering pancreatic islet function, reducing appetite, reducing food intake, and/or reducing calorie intake in a subject, comprising administering a therapeutically effective amount of an analogue of PYY according to the invention, or a pharmaceutical composition as defined in claims according to the invention to the subject.

According to a further aspect of the invention there is provided a method of preventing or treating diabetes and/or obesity in a subject, comprising administering a therapeutically effective amount of an analogue of PYY according to the invention, or a pharmaceutical composition according to the invention, to the subject.

In respect of all aspects of the invention, the subject may be overweight, obese and/or diabetic. Alternatively the subject may be of a healthy weight.

The PYY analogue or pharmaceutical composition according to the invention is administered parentally. According it may be provided in a format suitable for such administration. For example it may be provided in an injection device.

Preferably the PYY analogue or pharmaceutical composition is administered subcutaneously and may be provided in a format suitable for such administration.

According to a further aspect of the invention there is provided a method of causing weight loss or preventing weight gain in a subject for cosmetic purposes, comprising administering an effective amount of an analogue of PYY according to the invention, to the subject. The subject in such cases may be obese, overweight or according to some preferred embodiments of healthy weight.

Peptide hormone analogues of the invention may be produced by recombinant methods well known in the art or alternatively they may be produced by synthetic methods, again well known in the art.

PYY analogues according to the present invention preferably have a more sustained effect on food intake reduction or have a stronger effect on food intake reduction than human PYY. Preferably they have an effect on food intake reduction which is at least as strong as native human PYY but which is more sustained. Increased duration of appetite suppression can be particularly important to avoid the effect known as "escape". A short duration of appetite suppressant may reduce appetite or the time covered by one meal and in that meal the subject typically eats less food. If, however, the appetite suppressant is then metabolized or otherwise removed from circulation as a subject then by the time the next meal the subject can regain its "normal" appetite. In view of the subject having eaten a small meal at the previous mealtime, the subject may in fact have an increased appetite at the time of the second meal. If the subject satisfies that appetite it is possible for the food intake over the two meals in total to be no lower than the food intake would have been without the appetite suppressant. That is to say, the subject may have "escaped" from the effects of the appetite suppressant. "Escape" can be reduced by using additional doses of appetite suppressant or by using an appetite suppressant with a longer duration of action. If the subject has a reduced appetite for longer, then the degree to which it can make up the deficit from one meal in the next meal is reduced and as there is a practical limit to total capacity in a particular single meal.

Preferably the PYY analogues of the invention are selective for the Y2 receptor. That is to say, they bind with a higher affinity to Y2 compared with other receptors such as Y1, Y3, Y4, Y5 and Y6. Those receptors are recognized based on binding affinity, pharmacology and sequence. Most, if not all, of the receptors are G protein coupled receptors. The Y1 receptor is generally considered to be postsynaptic and mediates many of the known actions of neuropeptide Y in the periphery. Originally, this receptor was described as having poor affinity for C-terminal fragments of neuropeptide Y, such as the 13-36 fragment, but interacts with the full length neuropeptide Y and peptide YY with equal affinity (see PCT publication WO 93/09227).

Pharmacologically, the Y2 receptor is distinguished from Y1 by exhibiting affinity for C-terminal fragments of neuropeptide Y. The Y2 receptor is most often differentiated by the affinity of neuropeptide Y(13-36), although the 3-36 fragment of neuropeptide Y and peptide YY provides improved affinity and selectivity (see Dumont et al., *Society for Neuroscience Abstracts* 19:726, 1993). Signal transmission through both the Y1 and the Y2 receptors are coupled to the inhibition of adenylate cyclase. Binding to the Y2 receptor was also found to reduce the intracellular levels of calcium in the synapse by selective inhibition of N-type calcium channels. In addition, the Y2 receptor, like the Y1 receptors, exhibits differential coupling to second messengers (see U.S. Pat. No. 6,355,478). Y2 receptors are found in a variety of brain regions, including the hippocampus, substantia nigra-lateralis, thalamus, hypothalamus, and brainstem. The human, murine, monkey and rat Y2 receptors have been cloned (e.g., see U.S. Pat. Nos. 6,420,352 and 6,355,478). Preferably the PYY analogue of the invention binds to Y2 with an affinity that is at least two-fold, at least five-fold, or at least ten-fold greater than the binding affinity for Y1, Y3, Y4, Y5 and/or Y6.

An analogue of PYY according to the invention preferably has low or no net ionic charge in solution (i.e., in a solution approximating to physiological conditions, such as, for example, those found in the tissue fluid or plasma, such as at pH 7.4), e.g. preferably the PYY analogue of the invention has a net ionic charge at pH 7.4 of +1, 0, or −1. For example, a PYY analogue having two acidic groups and two basic groups will have a net ionic charge of 0. An acidic group which has a pKa in water of less than 6.4 is considered as contributing an ionic charge of −1 at pH 7.4. A basic group which has a pKa of more than 8.4 is considered as contributing an ionic charge of +1 at pH 7.4. It is hypothesised that low net ionic charge, and particularly an absence of net ionic charge under in vivo conditions, limits in vivo solubility of the PYY analogue, and that this contributes to a slower absorption after subcutaneous administration of a high concentration peptide and thus prolonged presence in the circulation.

PYY analogues according to the invention contain histidine at position 26, as is the case for native PYY. PYY analogues according to the invention preferably also contain His at position 19 and/or 30. According to one preferred aspect of the invention, analogues of PYY according to the invention further contain at least one of the amino acids corresponding to positions 19 and 30 in the native PYY molecule substituted for histidine. More preferably, the amino acid at position 30 of the PYY analogue is histidine.

In one particularly preferred embodiment, the PYY analogue of the invention contains 3 histidine residues, at positions 19, 26 and 30.

By way of further explanation, histidine is a unique amino acid in being not charged at pH 7.4 (i.e. under physiological conditions in the circulation or subcutaneously following subcutaneous administration). However, it is fully charged at pH 5 (or lower) since the pI of the NH side chain of histidine is about 6.0. According to certain preferred embodiments an analogue of PYY according to the invention has low or no overall charge at physiological pH (pH 7.4) and is preferably formulated as part of a composition having a pH of about pH5 (for example from pH 4.5 to pH 6.0—a lower pH than approximately pH 4 or 5 may be undesirable for an injectable composition because it is likely to increase pain at the injection site) so as to exhibit histidine ionisation and preferably an overall net change at such a lower pH. An increase in the number of charged residues increases the solubility of an injectable composition in the vial and therefore allows a small volume injection of a relatively concentrated peptide solution to be given. However, subsequent to subcutaneous injection the analogue is exposed to physiological pH at which the number of ionised residues and especially the number of ionised histidine residues falls and therefore solubility decreases. This causes the peptide to precipitate subcutaneously.

The presence of His residues enhances this effect.

According to certain preferred embodiments, PYY analogues according to the invention have a combination of the following preferred features:

1) A peptide sequence which at pH 7.4 has no or low net ionic charge (e.g. +1, 0, or −1) and may have relatively few charged groups and hydrophilic groups overall to decrease intrinsic solubility.
2) The presence of a number of histidines which produce a net positive charge and good solubility at pH 5 for storage before administration and to allow a low viscosity administration solution (at pH 5).
3) Suitability for subcutaneous administration of a low volume and high concentration, exceeding the solubility constant at pH 7.4 but not at pH 5.

In addition to histidine being a particularly advantageous amino acid residue for causing this differential pH-dependent solubility effect, the differential solubility of peptides containing histidine residues is greatly enhanced if formulated together with zinc ions. This is because zinc ions will bind to uncharged histidine residues in aqueous solution. It is believed that zinc ions are able to bind simultaneously to up to 4 uncharged histidines. This allows zinc to co-ordinate with histidine residues in several individual peptide molecules and thereby weakly cross-link the peptide molecule to other similar peptide molecules leading to a fall in solubility. However, zinc ions do not bind to charged histidine. Therefore, histidine containing peptides in a composition containing zinc ions will be cross-linked by weak ionic bonds at pH 7.4 but not at pH 5.0. The presence of His residues bound to zinc ions therefore enhances precipitation of the peptide after subcutaneous injection but does not affect solubility in the vial or syringe before administration. This means that a peptide having an overall pI of approximately 7 will have no charged residues at approximately neutral pH and a peptide comprising histidine residues in a formulation including zinc ions is advantageously soluble in the vial or syringe but precipitates subcutaneously following administration. So a pH 7 neutral peptide with histidines in a formulation including zinc ions is advantageously soluble in the vial and syringe but precipitates subcutaneously following administration. Furthermore, zinc-enhanced precipitation is gradually reversible because the concentration of zinc ions following injection will fall as zinc ions are gradually washed out of the injection site. Therefore there is observed a delay in subcutaneous absorption with much better pharmacokinetics but no loss of bio-availability. The rate of absorption for a given histidine-containing neutral peptide can be controlled by the amount of zinc added.

Introduction of at least one additional histidine residue preferably results in the PYY analogues of the invention having at least one occurrence of two histidine residues separated from each other by 1 to 3 intervening amino acid residues (a pair of histidine residues). Such a spacing appears to be optimum for a single zinc ion to form in aqueous solution associations with both histidine residues in a pair. In one advantageous embodiment of the invention the amino acid residues at positions 26 and 30 are each histidine residues.

Preferably an analogue according to the invention has an overall pI of between 6.5 and 8.5. This means that at physiological pH (e.g. pH 7.4) the analogue has no low or no significant overall charge (e.g. as mentioned above, preferably the PYY analogue of the invention has a net ionic charge at pH 7.4 of +1, 0, or −1). The overall pI of a molecule may be calculated using techniques well known to a person skilled in the art or alternatively may be determined experimentally by using isoelectric focusing.

In order to take full advantage of this effect the inventors have found that the following combination of features are particularly preferred.

1) Peptide sequence which at pH 7.4 has low or no net ionic charge (e.g. +1, 0, or −1).
2) Presence of three histidines which produce a net positive charge and good solubility at pH 5 for storage before administration.
3) High solubility at pH 5 which allows for subcutaneous administration of a therapeutic dose of the PYY analogue in a low volume of aqueous medium, and low solubility at pH 7.4.
4) The presence of zinc ions which produce cross-linking of uncharged histidine residues at pH 7.4 and adjacent molecules but which do not cross-link charge histidine at pre-administration pH or approximately pH 5.

It is found that analogues having a His residue at positions 19 and 30 may be especially advantageous and therefore to be preferred. The Inventors have found that, despite the last six amino acids of the sequence being thought to be important for the activity of the compound, the native Leu30 can be substituted for His30 without loss of activity.

Accordingly, according to certain preferred embodiments, there is provided an analogue of PYY which differs from the sequence of native PYY in the following respects:

Ser23 is substituted with Ala23, Glu23, Lys23, Gln23 for AIB23 (preferably Ala23)

Arg19 is substituted with His19

Leu30 is substituted with His30

Such a compound may further differ from the sequence of native human PYY in one or more of the following respects:

Tyr is absent

One or more of residues 2, 4, 6, 7, 9, 13, 15, 16, 20, 21, 24, 25 or 26 are subject to a conservative substitution Glu10 is substituted with Ala10, Lys10 or Gln10

Asp11 is substituted with Gly11

Ala12 is substituted with AIB12

Leu17 is substituted with Ile17 or AIB17

Asn18 is substituted with AIB18, Ala18 or Leu18 (preferably Leu18)

Ala22 is substituted with Val22 or Ile22

Tyr27 is substituted with Phe27

Val31 is substituted with Leu31 and wherein the C-terminal residue optionally terminates in a primary amide (—C(O)NH$_2$) group in place or a carboxylic acid group (—CO$_2$H); or a derivative of the compound; or a salt of the compound or the derivative.

Preferably residues 2, 4, 6, 7, 9, 13, 15, 16, 20, 21, 24, 25 and 26 are not substituted.

Derivatives

A PYY analogue of the invention may be a derivative as a consequence of being modified by well-known processes including amidation, glycosylation, carbamylation, acylation, for example acetylation, sulfation, phosphorylation, cyclization, lipidization, pegylation and fusion to another peptide or protein to form a fusion protein. A PYY analogue of the invention may be modified at random positions within the molecule, or at predetermined positions within the molecule and may include one, two, three or more attached chemical moieties.

A PYY analogue of the invention may be a fusion protein, whereby the analogue is fused to another protein or polypeptide (the fusion partner) using recombinant methods known in the art. Alternatively, such a fusion protein may be synthetically synthesized by any known method. Any suitable peptide or protein can be used as the fusion partner (e.g., serum albumin, carbonic anhydrase, glutathione-S-transferase or thioredoxin, etc.). Preferred fusion partners will not have an adverse biological activity in vivo. Such fusion proteins may be made by linking the carboxy-terminus of the fusion partner to the amino-terminus of the PYY analogue or vice versa. Optionally, a cleavable linker may be used to link the PYY analogue to the fusion partner. A resulting cleavable fusion protein may be cleaved in vivo such that an active form of a compound of the invention is released. Examples of such cleavable linkers include, but are not limited to, the linkers D-D-D-D-Y, G-P-R, A-G-G and H-P-F-H-L, which can be cleaved by enterokinase, thrombin, ubiquitin cleaving enzyme and renin, respectively. See, e.g., U.S. Pat. No. 6,410,707, the contents of which are incorporated herein by reference. According to certain embodiments of all aspects of the invention, the PYY analogue is not a fusion protein.

A PYY analogue of the invention may be a physiologically functional derivative. The term "physiologically functional derivative" is used herein to denote a chemical derivative of a PYY analogue of the invention having the same physiological function as the corresponding unmodified PYY analogue of the invention. For example, a physiologically functionally derivative may be convertible in the body to a PYY analogue of the invention. According to the present invention, examples of physiologically functional derivatives include esters, amides, and carbamates; preferably esters and amides.

Pharmaceutically acceptable esters and amides of the compounds of the invention may comprise a C$_{1-20}$ alkyl-, C$_{2-20}$ alkenyl-, C$_{5-10}$ aryl-, C$_{5-10}$ ar-C$_{1-20}$ alkyl-, or amino acid-ester or -amide attached at an appropriate site, for example at an acid group. Examples of suitable moieties are hydrophobic substituents with 4 to 26 carbon atoms, preferably 5 to 19 carbon atoms. Suitable lipid groups include, but are not limited to, the following: lauroyl (C$_{12}$H$_{23}$), palmityl (C$_{15}$H$_{31}$), oleyl (C$_{15}$H$_{29}$), stearyl (C$_{17}$H$_{35}$), cholate; and deoxycholate.

Methods for lipidization of sulfhydryl-containing compounds with fatty acid derivatives are disclosed in U.S. Pat. Nos. 5,936,092; 6,093,692; and 6,225,445. Fatty acid derivatives of a compound of the invention comprising a compound of the invention linked to fatty acid via a disulfide linkage may be used for delivery of a compound of the invention to neuronal cells and tissues. Lipidisation markedly increases the absorption of the compounds relative to the rate of absorption of the corresponding unlipidised compounds, as well as prolonging blood and tissue retention of the compounds. Moreover, the disulfide linkage in lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include, but are not limited to, the following: palmityl (C$_{15}$H$_{31}$), oleyl (C$_{15}$H$_{29}$), stearyl (C$_{17}$H$_{35}$), cholate; and deoxycholate.

Cyclization methods include cyclization through the formation of a disulfide bridge and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

A PYY analogue of the invention may be a pegylated structure of a PYY analogue. Pegylated compounds of the invention may provide additional advantages such as increased solubility, stability and circulating time of the polypeptide, or decreased immunogenicity (see U.S. Pat. No. 4,179,337).

Chemical moieties for derivitisation of a compound of the invention may also be selected from water soluble polymers such as polyethylene glycol, ethylene glycol/propylene glycol copolymers, carboxymethylcellulose, dextran, polyvinyl alcohol and the like. A polymer moiety for derivatisation of a compound of the invention may be of any molecular weight, and may be branched or unbranched. For ease in handling and manufacturing, the preferred molecular weight of a polyethylene glycol for derivatisation of a compound of the invention is from about 1 kDa to about 100 kDa, the term "about" indicating that in preparations of polyethylene glycol, some molecules will weigh more, some less, than the stated molecular weight. Polymers of other molecular weights may be used, depending on the desired therapeutic profile, for example the duration of sustained release desired, the effects, if any on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

In one embodiment, the PYY analogue of the invention is not a derivative.

Salts of PYY analogues of the invention that are suitable for use in a medicament are those wherein a counterion is pharmaceutically acceptable. However, salts having non-pharmaceutically acceptable counterions are within the scope of the present invention, for example, for use as intermediates in the preparation of PYY analogues of the invention and their pharmaceutically acceptable salts and/or derivatives thereof.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, lactic, salicylic, oxaloacetic, methanesulfonic, ethanesulfonic, p-toluenesulfonic, formic, benzoic, malonic, naphthalene-2-sulfonic, benzenesulfonic, and isethionic acids.

Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al, Pharmaceutical Research 12(7), 1995, 954-954, and Water-Insoluble Drug Formulation, $2^{nd}$ ed. R. Liu, CRC Press, page 553, which are incorporated herein by reference. Accordingly, it will be understood by the skilled person that PYY analogues of the invention, as well as derivatives and/or salts thereof may therefore be present in the form of solvates. Solvates of PYY analogues of the invention which are suitable for use in medicine are those wherein the associated solvent is pharmaceutically acceptable. For example, a hydrate is an example of a pharmaceutically acceptable solvate.

Conditions

The invention also provides an analogue of PYY according to the invention, or a pharmaceutical composition comprising the analogue of PYY, for use as a medicament. The PYY analogue and pharmaceutical composition find use in the treatment and/or prevention of conditions such as diabetes and obesity. The PYY analogue, and pharmaceutical composition comprising the PYY analogue, also find use in reducing appetite in a subject, reducing food intake in a subject, and/or reducing calorie intake in a subject.

The invention also provides the use of an analogue of PYY according to the invention for the manufacture of a medicament for the prevention or treatment of diabetes and/or obesity. The invention also provides the use of an analogue of PYY according to the invention for the manufacture of a medicament for reducing appetite in a subject, reducing food intake in a subject, and/or reducing calorie intake in a subject.

The invention also provides a method of treating or preventing a disease or disorder or other non-desired physiological state in a subject, comprising administering a therapeutically effective amount of an analogue of PYY according to the invention, or a pharmaceutical composition comprising the PYY analogue, to the subject.

The invention also provides a method of preventing or treating diabetes and/or obesity, reducing appetite, reducing food intake, and/or reducing calorie intake in a subject, comprising administering a therapeutically effective amount of an analogue of PYY according to the invention, or a pharmaceutical composition comprising the PYY analogue, to the subject.

In one embodiment, the PYY analogue or pharmaceutical composition is administered parentally. In one embodiment, the PYY analogue or pharmaceutical composition is administered subcutaneously. In one embodiment, the PYY analogue or pharmaceutical composition is administered intravenously, intramuscularly, intranasally, transdermally or sublingually.

The subject to whom the PYY analogue according to the invention, or pharmaceutical composition comprising the PYY analogue, is administered may be overweight, for example they may be obese. Alternatively, or in addition, the subject may be diabetic, for example having insulin resistance or glucose intolerance, or both. The subject may have diabetes mellitus, for example, the subject may have Type II diabetes. The subject may be overweight, for example, obese and have diabetes mellitus, for example, Type II diabetes. Alternatively, the subject may have Type I diabetes.

The PYY analogues of the invention are thought to protect islet of Langerhans cells, in particular beta cells, allowing them to retain their normal physiological function, for example the ability to secrete insulin in response to appropriate stimuli, when challenged by toxins (e.g. streptozotocin), pathogens or by an autoimmune response. The PYY analogues of the invention are also thought to be effective in recovering or rescuing pancreatic islet function, and, in particular, beta cell function, following deterioration of physiological function following exposure to a toxin, pathogen or an autoimmune response. Recovery of function may be to at least 10, 20, 30, 40, 50, 60, 70, 80, 90 or 100% of the function exhibited prior to deterioration. Accordingly, the invention also provides a PYY analogue of the invention, or a pharmaceutical composition comprising the PYY analogue, for use in preventing loss of pancreatic islet function (for example beta cell function) and/or recovering pancreatic islet function (for example beta cell function). The invention further provides the use of a PYY analogue of the invention for the manufacture of a medicament for preventing loss of pancreatic islet function (for example beta cell function) and/or for recovering pancreatic islet function (for example beta cell function). The invention further provides a method of preventing loss of pancreatic islet function (for example beta cell function) and/or recovering pancreatic islet function (for example beta cell function) in a subject comprising administering to the subject an effective amount of a PYY analogue of the invention, or a pharmaceutical composition comprising the PYY analogue, to the subject.

The pancreatic islet-protecting properties of the PYY analogues of the invention render them useful for administration in combination with further therapeutic agents which have as a side-effect islet toxicity. An example of such a therapeutic agent is steptozocin. Accordingly, the invention also provides a PYY analogue according to the invention in combination with a further therapeutic agent which has islet toxicity as a side-effect. The invention also provides a pharmaceutical composition comprising a PYY analogue according to the invention and a further therapeutic agent which has islet toxicity as a side-effect, together with a pharmaceutically acceptable carrier.

In addition, or alternatively, the subject may have, or may be at risk of having, a disorder in which obesity or being overweight is a risk factor. Such disorders include, but are not limited to, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acnthosis nigricans; eczema; exercise intolerance; insulin resistance; hypertension hypercholesterolemia; cholithiasis; osteoarthritis; orthopedic injury; insulin resistance, for example, type-2 diabetes and syndrome X; and thromboembolic disease (see Kopelman, *Nature* 404:635-43; Rissanen et al., *British Med. J.* 301, 835, 1990).

Other disorders associated with obesity include depression, anxiety, panic attacks, migraine headaches, PMS, chronic pain states, fibromyalgia, insomnia, impulsivity, obsessive compulsive disorder, and myoclonus. Furthermore, obesity is a recognized risk factor for increased incidence of complications of general anesthesia. (See e.g., Kopelman, *Nature* 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatitis; as well as abdominal hernias; acanthosis nigricans; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odors and infections in the skin folds under the breasts, etc .; large anterior abdominal wall masses, for example abdominal panniculitis with frequent panniculitis, impeding walking, causing frequent infections, odors, clothing difficulties, low back pain; musculoskeletal disease; pseudo tumor cerebri (or benign intracranial hypertension), and sliding hiatil hernia.

The present invention further provides a method for increasing energy expenditure in a subject. The method includes, for example, peripherally administering a therapeutically effective amount of a PYY analogue of the invention to the subject, thereby altering energy expenditure. Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat.

In one aspect, the method of the invention involves manipulation of the arcuate circuitry that alter food intake coordinately and reciprocally alter energy expenditure. Energy expenditure is a result of cellular metabolism, protein synthesis, metabolic rate, and calorie utilization. Thus, in this aspect of the invention, administration of a PYY analogue according to the invention results in increased energy expenditure, and decreased efficiency of calorie utilization.

The invention also provides a method for improving a lipid profile in a subject comprising administration of a PYY analogue according to the invention, or a pharmaceutical composition comprising the PYY analogue, to the subject. The invention also provides a method for alleviating a condition or disorder that can be alleviated by reducing nutrient availability, comprising administration of a PYY analogue according to the invention, or a pharmaceutical composition comprising the PYY analogue, to the subject.

Appetite can be measured by any means known to one of skill in the art. For example, decreased appetite can be assessed by a psychological assessment. For example, administration of a compound of the invention results in a change in perceived hunger, satiety, and/or fullness. Hunger can be assessed by any means known to one of skill in the art. For example, hunger is assessed using psychological assays, such as by an assessment of hunger feelings and sensory perception using a questionnaire, such as, but not limited to, a Visual Analog Score (VAS) questionnaire. In one specific, non-limiting example, hunger is assessed by answering questions relating to desire for food, drink, prospective food consumption, nausea, and perceptions relating to smell or taste.

A PYY analogue of the invention may be used for weight control and treatment, for example reduction or prevention of obesity, in particular any one or more of the following: preventing and reducing weight gain; inducing and promoting weight loss; and reducing obesity as measured by the Body Mass Index. A PYY analogue of the invention may be used in the control of any one or more of appetite, satiety and hunger, in particular any one or more of the following: reducing, suppressing and inhibiting appetite; inducing, increasing, enhancing and promoting satiety and sensations of satiety; and reducing, inhibiting and suppressing hunger and sensations of hunger. A PYY analogue of the invention may be used in maintaining any one or more of a desired body weight, a desired Body Mass Index, a desired appearance and good health. Accordingly, the invention also provides a method of causing weight loss or preventing weight gain in a subject for cosmetic purposes, comprising administering an effective amount of an analogue of PYY according to the invention, or a composition comprising the PYY analogue, to the subject.

A subject may be a subject who desires weight loss, for example female and male subjects who desire a change in their appearance. A subject may desire decreased feelings of hunger, for example the subject may be a person involved in a lengthy task that requires a high level of concentration, for example soldiers on active duty, air traffic controllers, or truck drivers on long distance routes, etc.

The present invention may also be used in treating, prevention, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

The invention relates to the treatment of metabolic disorders, for example disorders of energy metabolism. Such disorders include conditions or disorders associated with increased caloric intake include, but are not limited to, insulin resistance, glucose intolerance, obesity, diabetes, including type-2 diabetes, eating disorders, insulin-resistance syndromes, and Alzheimer's disease.

According to the present invention, the PYY analogue is preferably used in the treatment of a human. However, while the compounds of the invention will typically be used to treat human subjects they may also be used to treat similar or identical conditions in other vertebrates for example other primates; farm animals for example swine, cattle and poultry; sport animals for example horses; companion animals for example dogs and cats.

Compositions

While it is possible for the active ingredient to be administered alone, it is preferable for it to be present in a pharmaceutical formulation or composition. Accordingly, the invention also provides a pharmaceutical composition comprising an analogue of PYY according to the invention together with a pharmaceutically acceptable carrier and optionally other therapeutic ingredients. Pharmaceutical compositions of the invention may take the form of a pharmaceutical formulation as described below.

The pharmaceutical formulations according to the invention include those suitable for oral, parenteral (including subcutaneous, intradermal, intramuscular, intravenous, and intraarticular), inhalation (including fine particle dusts or mists which may be generated by means of various types of metered dose pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Preferably, compositions according to the invention are suitable for subcutaneous administration, for example by injection. According to certain embodiments the composition may contain metal ion for example copper, iron, aluminium, zinc, nickel or cobalt ions. The presence of such ions may limit solubility and thus delay absorption into the circulatory system from the site of subcutaneous administration. In a particularly preferred embodiment, the composition contains zinc ions. Zinc ions may be present at any suitable concentration for example at a molar ratio to peptide molecules of 10:1 to 1:10, 8:1 to 1:8, 5:1 to 1:5, 4:1 to 1:4, 3:1 to 1:3, 2:1 to 1:2 or 1:1. In one embodiment, the pharmaceutical composition has a pH of less than 5 and the pharmaceutical composition comprises zinc ions.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. PYY analogues of the invention or variants, derivatives, salts or solvates thereof can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include oxidizing agents and other compounds that are known to be deleterious to PYY and related molecules. Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

In one embodiment, the pharmaceutical composition is present in a syringe or other administration device for subcutaneous administration to humans.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the PYY analogue.

It should be understood that in addition to the ingredients particularly mentioned above, the formulations of this invention may include other agents conventional in the art having regard to the type of formulation in question, for example those suitable for oral administration may include flavouring agents.

The PYY analogues of the invention are also suitably administered as sustained-release systems. Suitable examples of sustained-release systems of the invention include suitable polymeric materials, for example semi-permeable polymer matrices in the form of shaped articles, e.g., films, or mirocapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracistemally; intravaginally; intra-peritoneally; topically, for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the compound of formula (I). These compositions exhibit certain biocompatibility features which allow a controlled release of the active substance. See U.S. Pat. No. 5,700,486.

A PYY analogue of the invention may be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by a continuous subcutaneous infusions, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer (*Science* 249:1527-1533, 1990). In another aspect of the disclosure, compounds of the invention are delivered by way of an implanted pump, described, for example, in U.S. Pat. Nos. 6,436,091; 5,939,380; 5,993,414.

Implantable drug infusion devices are used to provide patients with a constant and long term dosage or infusion of a drug or any other therapeutic agent. Essentially such device may be categorized as either active or passive. A compound of the present invention may be formulated as a depot preparation. Such a long acting depot formulation can be administered by implantation, for example subcutaneously or intramuscularly; or by intramuscular injection. Thus, for example, the compounds can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of a PYY analogue of the invention may be administered as a single pulse dose, as a bolus dose, or as pulse doses administered over time. Thus, in pulse doses, a bolus administration of a PYY analogue of the invention is provided, followed by a time period wherein no a compound of the invention is administered to the subject, followed by a second bolus administration. In specific, non-limiting examples, pulse doses of a compound of the invention are administered during the course of a day, during the course of a week, or during the course of a month.

The invention also provides an analogue of PYY according to the invention together with a further therapeutic agent, for simultaneous, sequential or separate administration. The invention also provides a pharmaceutical composition comprising the PYY analogue according to the invention and a further therapeutic agent. Examples of further therapeutic agents include an additional appetite suppressant, a food-intake-reducing, plasma glucose-lowering or plasma lipid-altering agent. Specific, non-limiting examples of an additional appetite suppressant include amfepramone (diethylpropion), phentermine, mazindol and phenylpropanolamine, fenfluramine, dexfenfluramine, and fluoxetine. As mentioned above, the PYY analogue of the invention can be administered simultaneously with the additional appetite suppressant, or it may be administered sequentially or separately. In one embodiment, the compound of the invention is formulated and administered with an appetite suppressant in a single dose.

A PYY analogue of the invention may be administered whenever the effect, e.g., appetite suppression, decreased food intake, or decreased caloric intake, is desired, or slightly before to whenever the effect is desired, such as, but not limited to about 10 minutes, about 15 minutes, about 30 minutes, about 60 minutes, about 90 minutes, or about 120 minutes, before the time the effect is desired.

The therapeutically effective amount of a PYY analogue of the invention will be dependent on the molecule utilized, the subject being treated, the severity and type of the affliction, and the manner and route of administration. For example, a therapeutically effective amount of a PYY analogue of the invention may vary from about 0.01 μg per kilogram (kg) body weight to about 1 g per kg body weight, for example about 0.1 μg to about 20 mg per kg body weight, for example about 1 μg to about 5 mg per kg body weight, or about 5 μg to about 1 mg per kg body weight.

In one embodiment of the invention, a PYY analogue of the invention may be administered to a subject at from 5 to 1000 nmol per kg bodyweight, for example at from 10 to 750 nmol per kg bodyweight, for example at from 20 to 500 nmol per kg bodyweight, in particular at from 30 to 240 nmol per kg bodyweight. For a 75 kg subject, such doses correspond to dosages of from 375 nmol to 75 μmol, for example from 750 nmol to 56.25 μmol, for example from 1.5 to 37.5 μmol, in particular from 2.25 to 18 μmol.

In an alternative embodiment, a PYY analogue of the invention may be administered to a subject at 0.5 to 135 picomole (pmol) per kg body weight, for example 5 to 100 picomole (pmol) per kg body weight, for example 10 to 90 picomole (pmol) per kg body weight, for example about 72 pmol per kg body weight. In one specific, non-limiting example, a PYY analogue of the invention is administered in a dose of about 1 nmol or more, 2 nmol or more, or 5 nmol or more. In this example, the dose of the PYY analogue of the invention is generally not more than 100 nmol, for example, the dose is 90 nmols or less, 80 nmols or less, 70 nmols or less, 60 nmols or less, 50 nmols or less, 40 nmols or less, 30 nmols or less, 20 nmols or less, 10 nmols or less. For example, a dosage range may comprise any combination of any of the specified lower dose limits with any of the specified upper dose limits. Thus, examples of non-limiting dose ranges of compounds of the invention are within the range of from 1 to 100 nmols, from 2 to 90 mols, from 5 to 80 nmols.

In one specific, non-limiting example, from about 1 to about 50 nmol of a PYY analogue of the invention is administered, for example about 2 to about 20 nmol, for example about 10 nmol is administered as a subcutaneous injection. The exact dose is readily determined by one of skill in the art based on the potency of the specific PYY analogue utilized, the route of delivery of the PYY analogue and the age, weight, sex and physiological condition of the subject.

Suitable doses of PYY analogue of the invention also include those that result in a reduction in calorie intake, food intake, or appetite, or increase in energy expenditure that is equivalent to the reduction in calorie intake, food intake, or appetite, or to increase the energy expenditure, caused by the normal postprandial level of PYY. Examples of doses include, but are not limited to doses that produce the effect demonstrated when the serum levels of PYY are from about 40 pM to about 60 pM, or from about 40 pM to about 45 pM, or about 43 pM.

The doses discussed above may be given, for example, once, twice, three-times or four-times a day. Alternatively, they may be give once every 2, 3 or 4 days. In a slow release formulation containing zinc, it may be possible to give a dose once every 3, 6, 7, 8, 9, 10, 11, 12, 13, 14, 15, 16, 17, 18, 19, 20 or 21 days. According to certain embodiments they may be administered once shortly before each meal to be taken.

Specific Sequences of the Invention

According to certain specific embodiments of the invention the analogue of PYY has an amino acid sequence given in one of the specific sequences set out in FIGS. 1A-1D.

The invention is illustrated by the following non-limiting Examples.

EXAMPLES

Materials and Methods

Peptide Synthesis

Peptides were made by a standard automated fluorenyl-methoxycarbonyl (Fmoc) solid phase peptide synthesis (SPPS) method. Peptide synthesis was carried out on a tricyclic amide linker resin. Amino acids were attached using the Fmoc strategy. Each amino acid was added sequentially from the C- to the N-termini. Peptide couplings were mediated by the reagent TBTU. Peptide cleavage from the resin was achieved with trifluoracetic acid in the presence of scavengers. Native PYY 3-36 $NH_2$ is obtained as described previously (WO03/026591); de novo synthesis using tricyclic amide resin and Fmoc chemistry is also possible.

Peptides were purified by reverse phase HPLC. Full quality control was performed on all purified peptides and peptides were shown to be greater than 95% pure by HPLC in two buffer systems. Amino acid analysis following acid hydrolysis confirmed the amino acid composition. MALDI-MS showed the expected molecular ion.

Binding Studies

Membrane preparation of HEK 293 cells overexpressing the human Y2 receptor (NPYR200000, Missouri S&T cDNA resource center) were isolated by osmotic lysis and differential centrifugation as described by Morgan et al (Neuroendocrinol 1996. 8 283-290). Receptor binding assays were completed as described by Druce et al (2009 Endocrinology 150(4) 712-22) except the buffer used was 0.02M HEPES pH 7.4, 5 mM $CaCl_2$, 1 mM $MgCl_2$, 1% bovine serum albumin, 0.1 mM diprotin A, 0.2 mM PMSF, 10 μM phosphoramidon, $^{125}I$-$PYY_{1-36}$ as the radiolabel and the human Y2 receptor used.

In Vitro Receptor Potency Studies

DiscoverX® hY2 CHO-K1 cells (10,000 cells per well (96 well plate)) were resuspended in media containing 0.2 mM IBMX and 0.02 mM forskolin (which stimulates cAMP production) and test peptides at a range of concentrations, for 30 minutes. The reaction stopped by lysing the cells and cAMP quantified 60 minutes later using Cisbio cAMP dynamic 2 kit. The peptides tested were "Y1419" falling within the scope of the present invention and having the sequence Pro-Ile-Lys-Pro-Glu-Ala-Pro-Gly-Glu-Gly-Ala-Ser-Pro-Glu-Glu-Leu-Leu-His-Tyr-Tyr-Ala-Ala-Leu-Arg-His-Phe-Leu-Asn-His-Val-Thr-Arg-Gln-Arg-Tyr-NH₂ (SEQ ID No:23) and a comparator peptide "Y242" having the sequence

```
                                    (SEQ ID NO: 44)
Pro-Ile-His-Pro-His-Ala-Pro-Gly-Glu-Asp-Ala-Ser-

Pro-Glu-Glu-Leu-Asn-His-Tyr-Tyr-Ala-Ala-Leu-Arg-

His-Tyr-Leu-Asn-His-Val-Thr-Arg-Gln-Arg-Tyr-NH₂.
```

Animals

Male Wistar rats (Charles River Ltd, Margate, UK) were used for animal experiments.

Feeding Studies in Rats

Rats were individually housed in IVC cages. Animals were randomised into treatment groups, with stratification by body weight. All peptide solutions were prepared freshly immediately prior to administration. The vehicle used for all studies was 5% v/v water and 95% NaCl (0.9% w/v). Peptide and vehicle were administered by subcutaneous injection with a dosage of either 25 or 50 nM/Kg body weight. Animals were injected every 24 hours over 6 days and the study continued for a further 24 hours giving 7 days total from the first injection to the end of the study. Animals were given free access to food and water during the study period. Animals were weighed at the end of the study and total weight loss, if any, was recorded.

Results

FIG. 1A discloses a number of specific sequences encompassed by the scope of the present invention in all its aspects. Each of these sequences is a specific embodiment of the invention. The number allocated to each sequence corresponds to the "Y" number referred to elsewhere herein (ie the line beginning with "1419" is understood to disclose the sequence of analogue number "Y1419") It also discloses, on the first line, the sequence of naturally occurring human PYY for reference.

The table below provides receptor potency data for the example peptides of FIGS. 1A-1D at the human Neuropeptide Y Receptor Y2 overexpressed in hY2 CHO-K1 cells (DiscoverX®). Ten thousand cells per well (96 well plate) were resuspended in media containing 0.2 mM IBMX and 0.02 mM forskolin (which stimulates cAMP production) and test peptides at a range of concentrations, for 30 minutes. The reaction stopped by lysing the cells and cAMP quantified 60 minutes later using Cisbio cAMP dynamic 2 kit. The values provided are the ratios of the example compound $EC_{50}$ to the $PYY_{2-36}$ $EC_{50}$ (e.g. for the "Average ratio to $PYY_{2-36}\pm SEM$" column, a value of 0.5 would indicate that the concentration of the example compound required to inhibit 50% maximum release of CAMP is half the concentration of $PYY_{2-36}$ that is required, and a value of 2 would indicate that the concentration of the example compound required to inhibit 50% maximum release of CAMP is 2 times that of $PYY_{2-36}$. It can be seen that example peptides of the invention are much more potent inhibitor than the previous generation of preferred compound (Y242 included in the table for comparative purposes).

| Peptide | Average ratio to $PYY_{2-36} \pm$ SEM |
|---------|--------------------------|
| Y242 | 10.0 ± 0.69 |
| Y1276 | 0.6 ± 0.06 |
| Y1319 | 0.6 ± 0.09 |
| Y1371 | 0.9 ± 0.06 |
| Y1372 | 1.1 ± 0.16 |
| Y1377 | 1.0 ± 0.07 |
| Y1379 | 0.9 ± 0.09 |
| Y1419 | 0.8 ± 0.16 |
| Y1421 | 0.9 ± 0.09 |
| Y1431 | 0.9 ± 0.07 |
| Y1447 | 1.4 ± 0.31 |
| Y1448 | 1.7 ± 0.46 |
| Y1450 | 1.1 ± 0.20 |
| Y1477 | 0.9 ± 0.06 |
| Y1489 | 1.0 ± 0.06 |
| Y1490 | 0.9 ± 0.28 |
| Y1518 | 1.7 ± 0.13 |
| Y1528 | 0.5 ± 0.08 |
| Y1553 | 0.8 ± 0.25 |
| Y1558 | 0.6 ± 0.05 |

FIG. 2 shows the differential ability of compound Y242 and compound Y1419 to inhibit forskolin production. It can be seen that 1419 is much more potent inhibitor than the previous generation of preferred compounds.

FIGS. 3A-3D and FIGS. 4A-4D show the results of rat feeding experiments comparing the activity of Y242 (FIGS. 3A-3D) and Y1419 (FIGS. 4A-4D) in overnight fasted male Wistar rats which have received a single subcutaneous injection of control saline or peptide in saline. Their food intake and body weight are monitored for the following 6 days and the values shown are the mean+/−SEM. It can be seen that although the comparator compound Y242 produced promising reductions in food intake and body weight for the first 48 hours, that reduction is not sustained for the longer time period (suggestion that the comparator compound although efficacious would need to be re-dosed after a day or two). Compound Y1419 performs much better and a single initial dose is still active at 160 hours after administration suggesting that the compound is promising for use as a medicine which would be administered weekly or less often.

FIGS. 5A-5D show the results of feeding experiments wherein fasted (24 h) male Wistar rats (Charles River) received a single subcutaneous injections of saline or example peptide of the invention (100 nmol/kg). Total food intake from dosing to 48 h after dosing was measured, as was body weight change from pre-fasted to 48 h post dose.

Figure 6B:
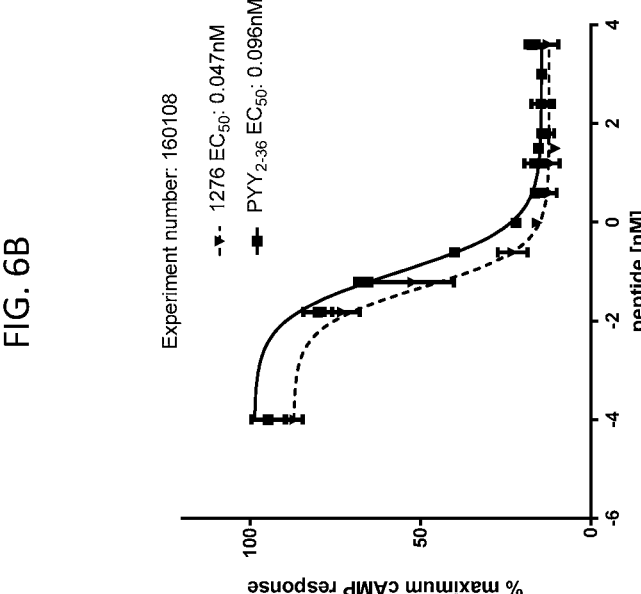
FIGS. 6A-6T show the results of an in vitro receptor potency experiment described in the examples
Figure 6A:
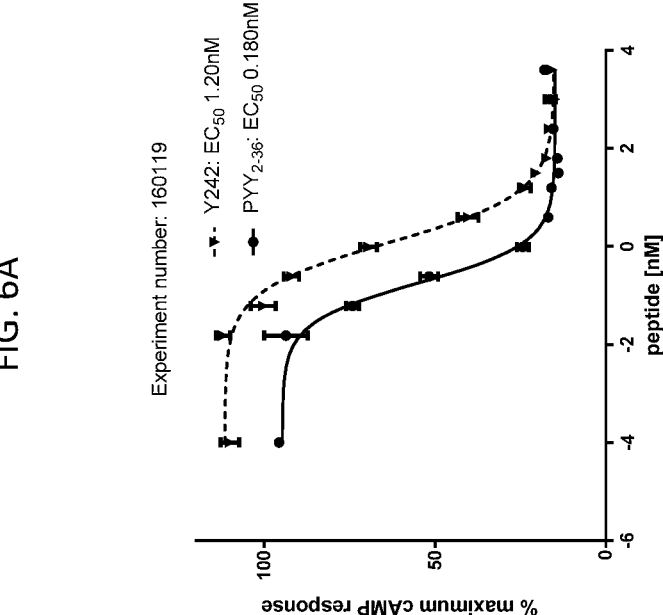
Figure 6D:
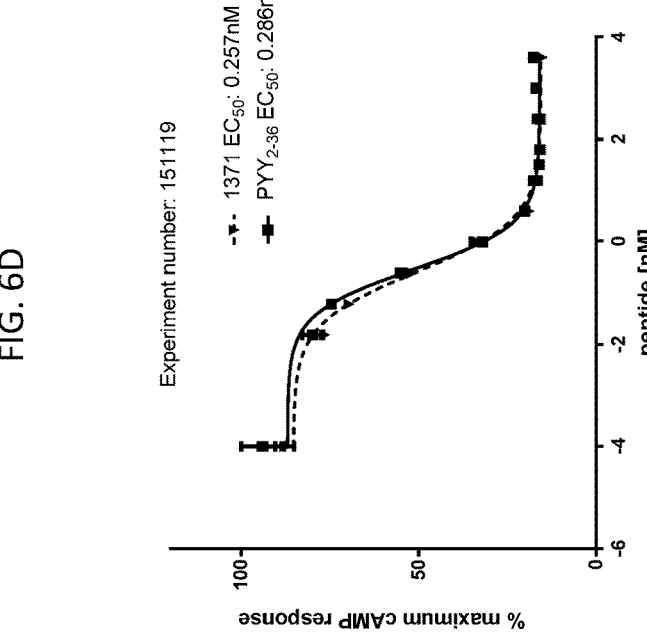
Figure 6C:
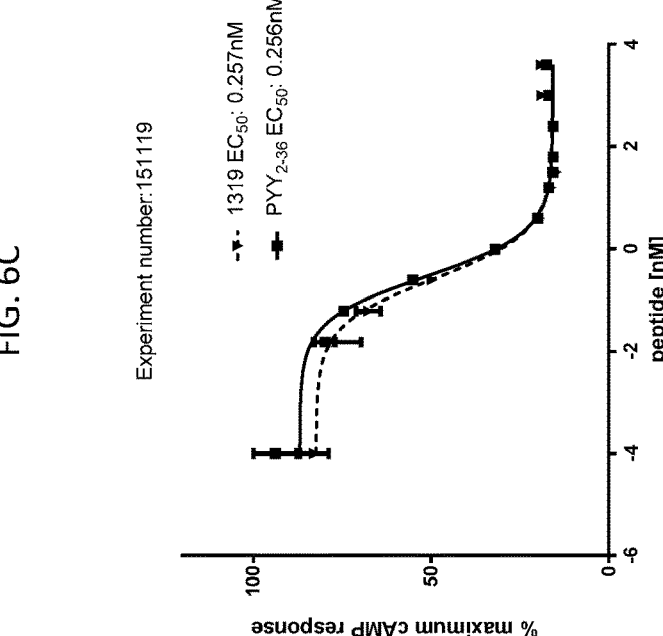
Figure 6F:
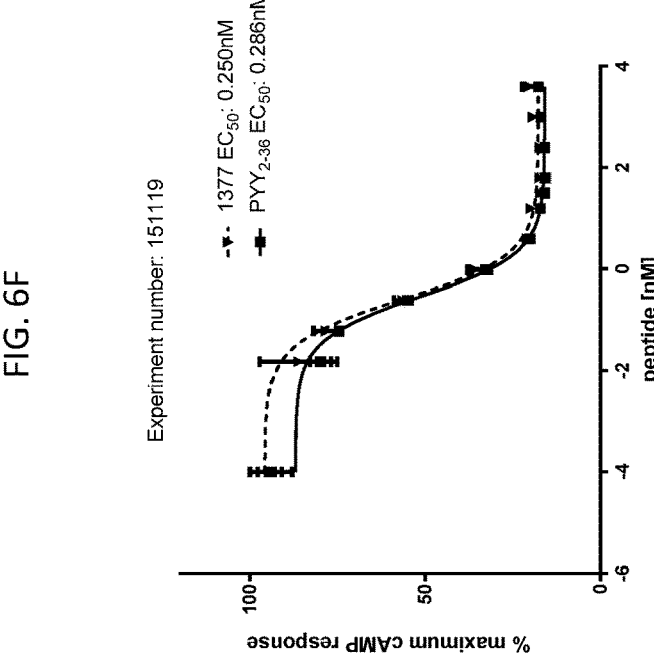
Figure 6E:
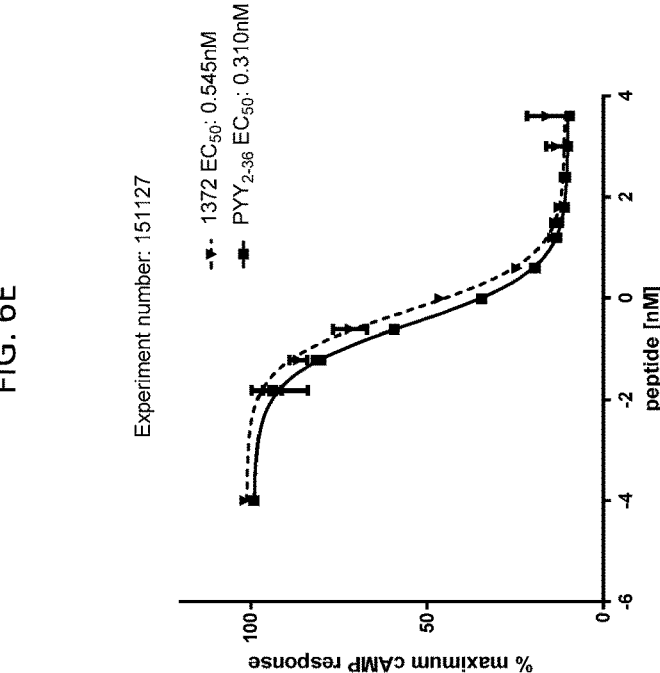
Figure 6H:
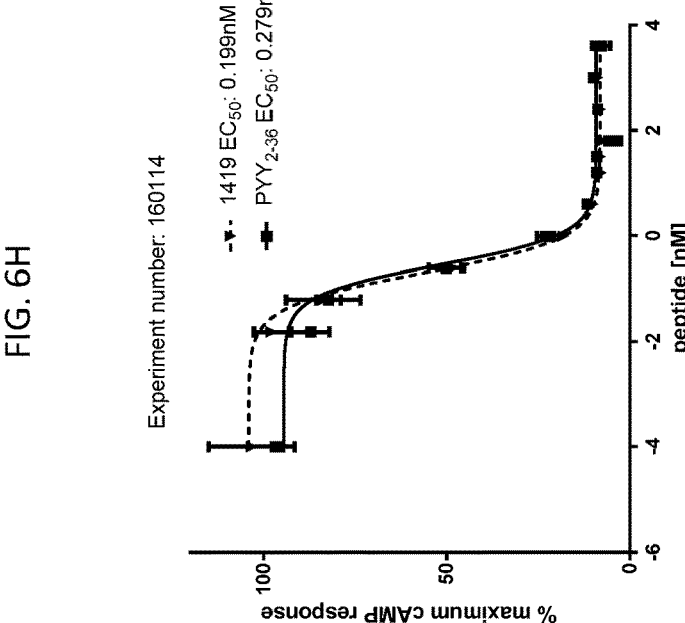
Figure 6G:
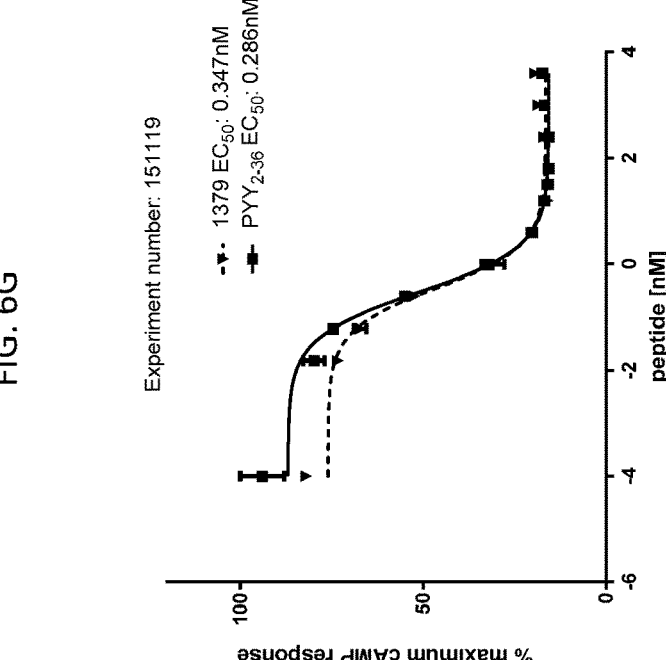
Figure 6J:
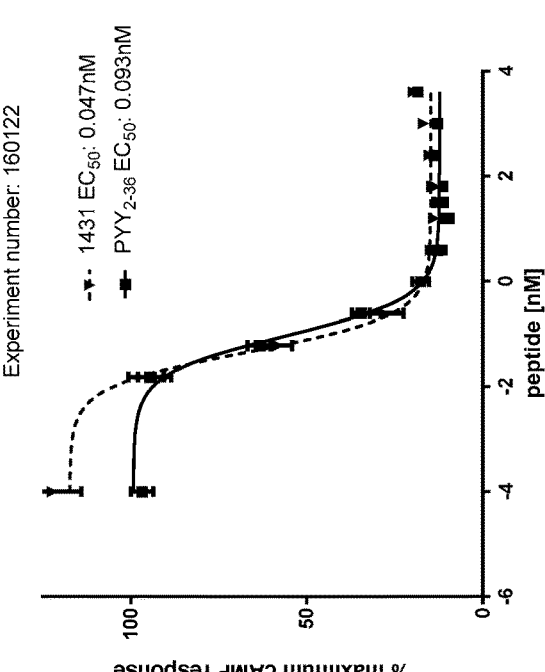
Figure 6I:
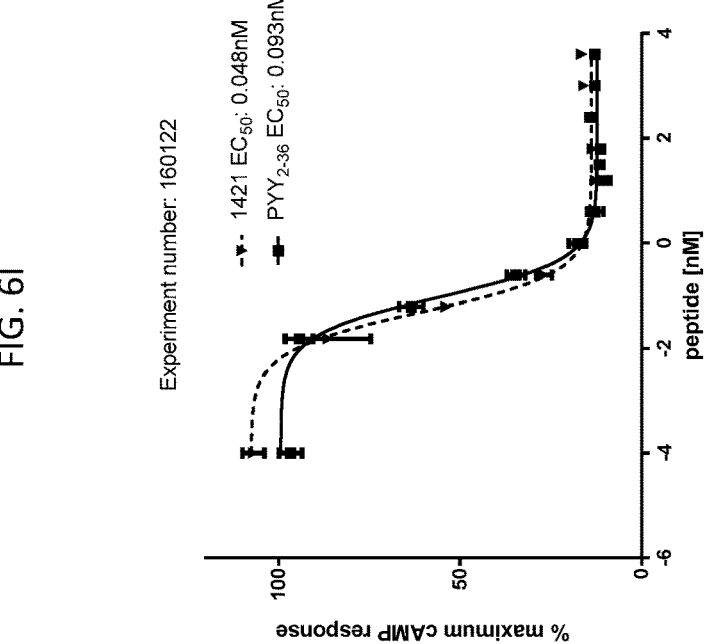
Figure 6L:
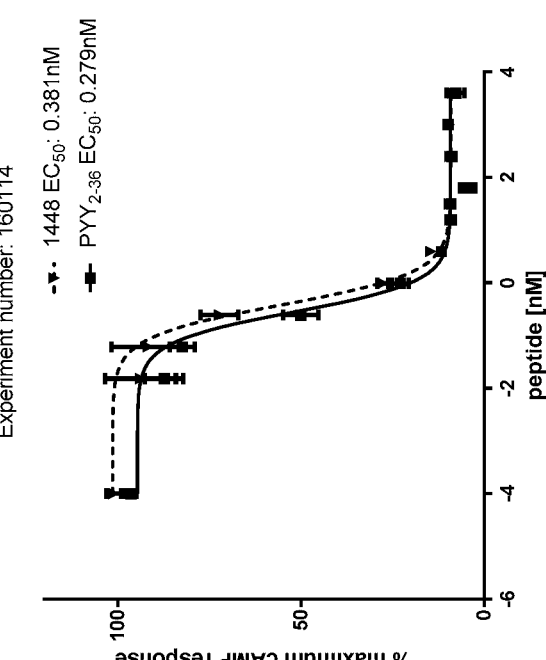
Figure 6K:
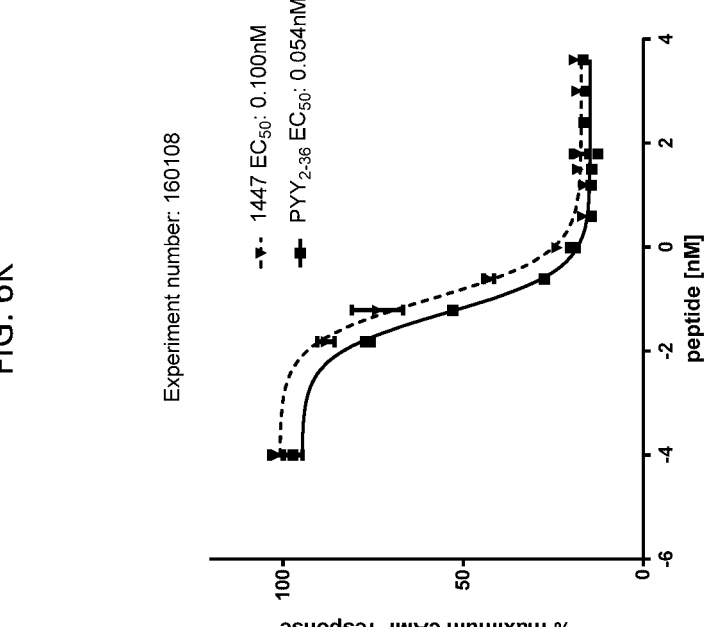
Figure 6N:
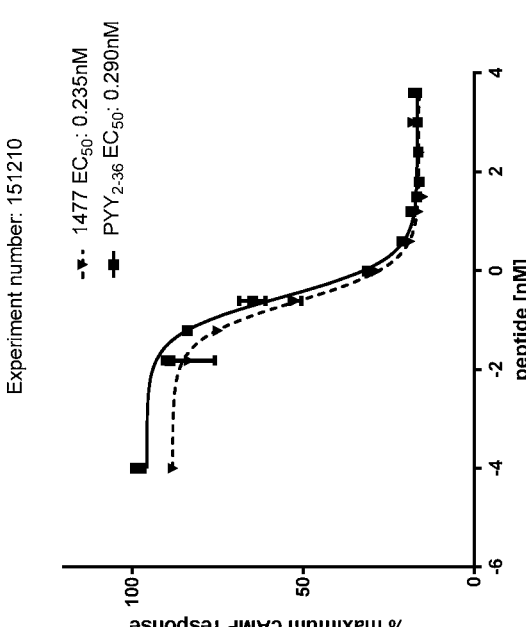
Figure 6M:
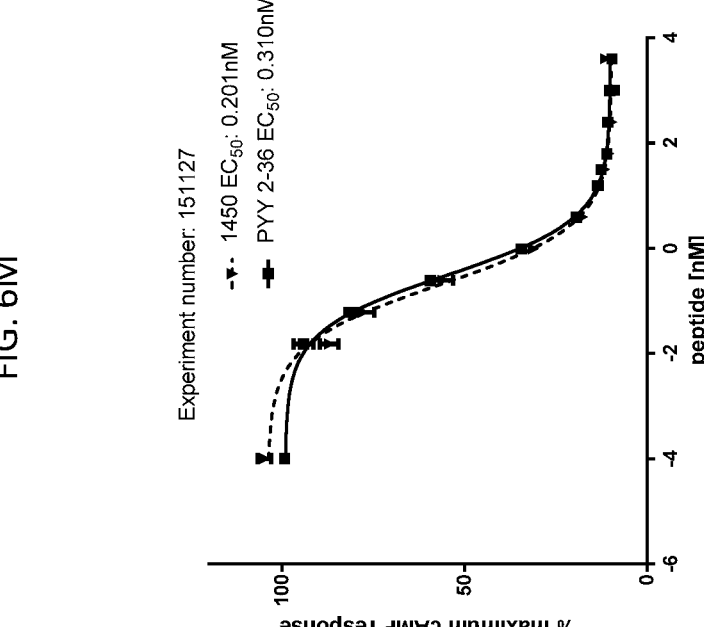
Figure 6P:
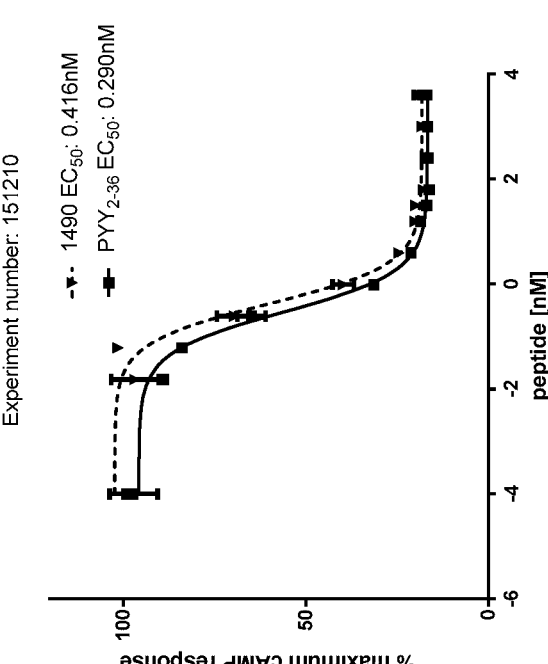
Figure 6O:
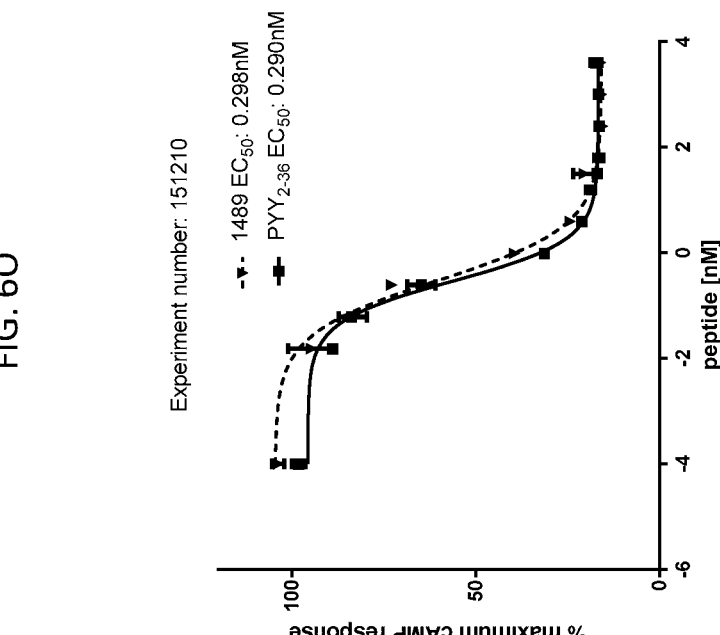
Figure 6R:
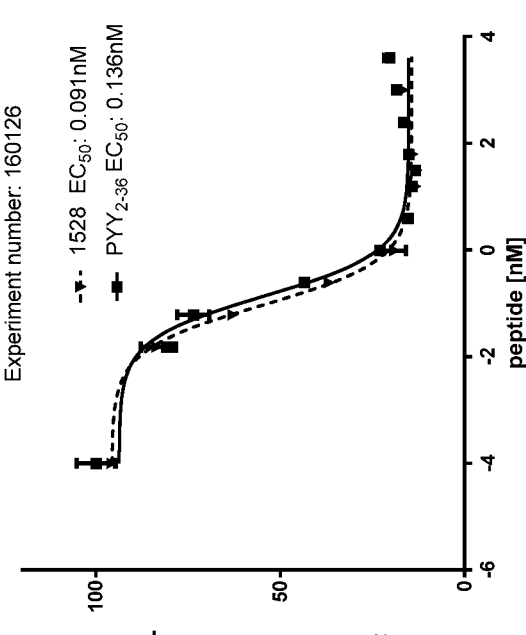
Figure 6Q:
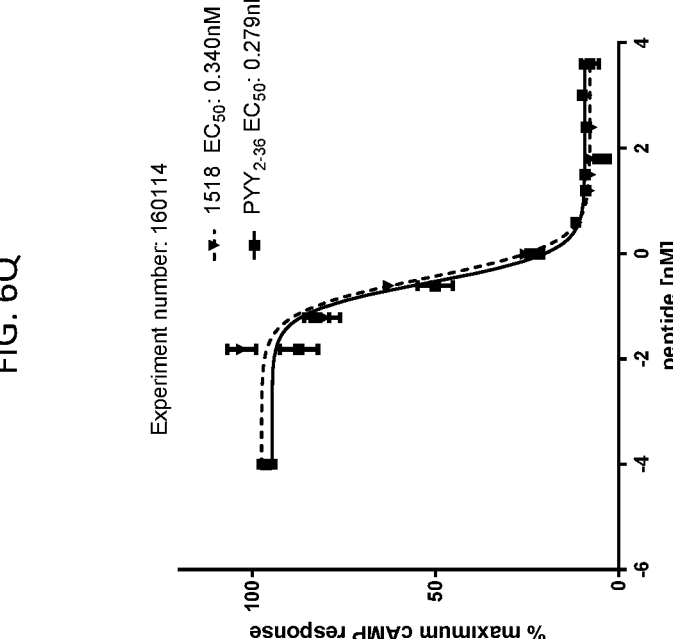
Figure 6T:
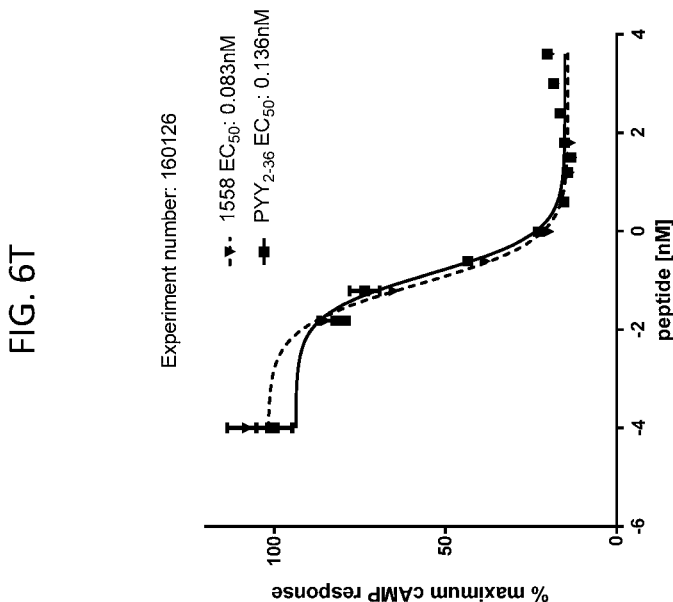
Figure 6S:
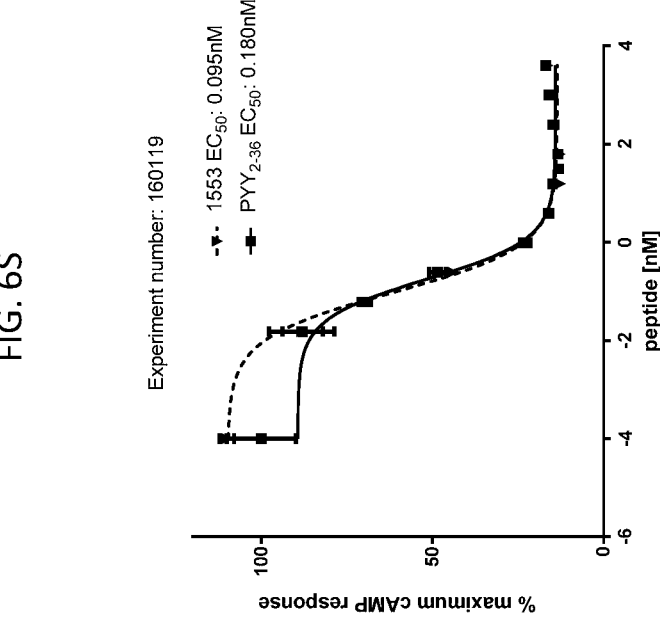

FIGS. 6A-6T show the ability of various indicated compounds of the invention to inhibit forskolin production. Data for PYY 2-36 is also included as a comparator.

The invention claimed is:

1. A method of causing weight loss or treating weight gain in a subject, comprising administering to the subject in need thereof a therapeutically effective amount of a) an analogue of PYY which differs from the sequence of native human PYY (SEQ ID NO: 1) in the following respects:

i Ser23 is substituted with Ala23, Glu23, or Aib23, ii Asn18 is substituted with Leu18, Aib18 or Ala18, and iii the analogue of PYY further differs from the sequence of native human PYY in at least one of the following respects:

Tyr1 is absent,

Glu10 is substituted with Lys10 or Gln10,

Asp11 is substituted with Gly11,

Arg19 is substituted with His19,

Tyr27 is substituted with Phe27,

Leu30 is substituted with His30, and

Val31 is substituted with Leu31, wherein

Lys4 is not substituted, and the C-terminal residue optionally terminates in a primary amide group (—C(O)NH$_2$) in place of a carboxylic acid group (—CO$_2$H); or b) a derivative of the analogue, wherein the derivative is selected from the group consisting of amidation, glycosylation, carbamylation, acylation, sulfation, phosphorylation, cyclization, lipidization, PEGylation, and fusion to another peptide or a protein to form a fusion protein; or c) a salt or solvate of the analogue or the derivative of the analogue.

2. The method of claim 1, wherein the C-terminal residue terminates in a primary amide group (—C(O)NH$_2$) in place of a carboxylic acid group (—CO$_2$H).

3. The method of claim 1, wherein Ser23 is substituted with Ala23.

4. The method of claim 1, wherein the analogue of PYY is selected from the group consisting of Y1372 (SEQ ID NO: 20), Y1419 (SEQ ID NO: 23), Y1421 (SEQ ID NO: 24), Y1518 (SEQ ID NO: 32), Y1528 (SEQ ID NO: 33), Y1558 (SEQ ID NO: 35), Y1568 (SEQ ID NO: 36), and Y1579 (SEQ ID NO: 41).

5. The method of claim 4, wherein the analogue of PYY is compound Y1419 (SEQ ID NO: 23).

6. The method of claim 1, wherein

Glu10 is unsubstituted,

Asn18 is substituted with Leu18, and

Ser23 is substituted with Ala23.

7. The method of claim 1, wherein

Asn18 is substituted with Leu18, and

Val31 is unsubstituted.

8. The method of claim 1, wherein the method comprises administering to the subject a therapeutically effective amount of a pharmaceutical composition comprising the analogue of PYY or derivative thereof together with a pharmaceutically acceptable carrier, and optionally a further therapeutic agent.

9. The method of claim 8, wherein the further therapeutic agent is selected from an analogue of GLP-1, an analogue of glucagon, and a derivative of either thereof.

10. The method of claim 8, wherein the pharmaceutical composition further comprises Zn2+ ions.

11. The method of claim 1, wherein the subject is overweight, obese, diabetic, or of a healthy weight.

12. The method of claim 11, wherein the subject is diabetic, the subject has Type II diabetes, or the subject has Type I diabetes.

13. The method of claim 1, wherein the administration is parental.

14. The method of claim 1, wherein the administration is subcutaneous.

15. The method of claim 4, wherein the analogue of PYY is compound Y1372 (SEQ ID NO: 20).

16. The method of claim 4, wherein the analogue of PYY is compound Y1421 (SEQ ID NO: 24).

17. The method of claim 4, wherein the analogue of PYY is compound Y1518 (SEQ ID NO: 32).

18. The method of claim 4, wherein the analogue of PYY is compound Y1528 (SEQ ID NO: 33).

19. The method of claim 4, wherein the analogue of PYY is compound Y1558 (SEQ ID NO: 35).

20. The method of claim 4, wherein the analogue of PYY is compound Y1568 (SEQ ID NO: 36).

21. The method of claim 4, wherein the analogue of PYY is compound Y1579 (SEQ ID NO: 41).

* * * * *